(12) United States Patent
Louwagie

(10) Patent No.: US 11,845,991 B2
(45) Date of Patent: Dec. 19, 2023

(54) FECAL SAMPLE PROCESSING AND ANALYSIS COMPRISING DETECTION OF BLOOD

(71) Applicant: Exact Sciences Corporation, Madison, WI (US)

(72) Inventor: Joost Louwagie, Dornach (CH)

(73) Assignee: Exact Sciences Corporation, Madison, WI (US)

( * ) Notice: Subject to any disclaimer, the term of this patent is extended or adjusted under 35 U.S.C. 154(b) by 903 days.

(21) Appl. No.: 15/634,607

(22) Filed: Jun. 27, 2017

(65) Prior Publication Data

US 2017/0298448 A1 Oct. 19, 2017

Related U.S. Application Data

(63) Continuation of application No. 15/010,436, filed on Jan. 29, 2016, now abandoned, which is a continuation of application No. 13/147,570, filed as application No. PCT/GB2010/000180 on Feb. 3, 2010, now abandoned.

(60) Provisional application No. 61/149,581, filed on Feb. 3, 2009.

(51) Int. Cl.
*C12Q 1/6886* (2018.01)
*G01N 33/574* (2006.01)

(52) U.S. Cl.
CPC ..... *C12Q 1/6886* (2013.01); *G01N 33/57446* (2013.01); *C12Q 2600/106* (2013.01); *C12Q 2600/154* (2013.01); *C12Q 2600/158* (2013.01); *G01N 2333/805* (2013.01); *G01N 2800/50* (2013.01); *G01N 2800/52* (2013.01)

(58) Field of Classification Search
CPC .................................................. G01N 33/574
See application file for complete search history.

(56) References Cited

U.S. PATENT DOCUMENTS

| | | | |
|---|---|---|---|
| 4,437,975 A | 3/1984 | Gillespie et al. | |
| 4,445,235 A * | 5/1984 | Slover | A61B 10/0038 4/144.1 |
| 4,582,811 A | 4/1986 | Pucci et al. | |
| 4,683,197 A | 7/1987 | Gallati | |
| 4,859,610 A | 8/1989 | Maggio | |
| 4,889,818 A | 12/1989 | Gelfand et al. | |
| 5,137,806 A | 8/1992 | Lemaistre et al. | |
| 5,196,167 A | 3/1993 | Guadagno et al. | |
| 5,198,365 A * | 3/1993 | Grow | G01N 33/528 436/17 |
| 5,527,676 A | 6/1996 | Vogelstein et al. | |
| 5,741,650 A | 4/1998 | Lapidus et al. | |
| 5,952,178 A | 9/1999 | Lapidus et al. | |
| 6,410,276 B1 | 6/2002 | Burg et al. | |
| 6,761,702 B2 * | 7/2004 | Smith | A61M 1/774 604/35 |
| 7,288,413 B2 | 10/2007 | Goulden | |
| 7,371,527 B1 | 5/2008 | Bayun et al. | |
| 8,969,046 B2 * | 3/2015 | Van Engeland | C12Q 1/6886 435/91.2 |
| 11,634,781 B2 | 4/2023 | Louwagie | |
| 2002/0096469 A1 | 7/2002 | Faulkner | |
| 2002/0187476 A1 | 12/2002 | Koroulis et al. | |
| 2003/0086869 A1 * | 5/2003 | Stallings | C12Q 1/44 424/9.1 |
| 2003/0096244 A1 * | 5/2003 | Rabello | C12Q 1/6888 435/7.22 |
| 2004/0019298 A1 * | 1/2004 | Zhou | A61B 10/0096 600/564 |
| 2004/0091881 A1 | 5/2004 | Olek et al. | |
| 2005/0064401 A1 * | 3/2005 | Olek | C07K 14/4703 435/6.12 |
| 2005/0075543 A1 * | 4/2005 | Calabrese | G16H 10/40 600/300 |
| 2005/0244836 A1 | 11/2005 | Tsang | |
| 2006/0084054 A1 * | 4/2006 | Alsobrook | C07K 14/47 435/6.14 |
| 2006/0188939 A1 * | 8/2006 | Gao | A61B 10/0038 435/7.1 |
| 2006/0210448 A1 * | 9/2006 | Wang | A61B 10/0038 422/400 |
| 2006/0216830 A1 * | 9/2006 | Kikuiri | B01L 3/5082 436/165 |
| 2007/0017015 A1 * | 1/2007 | Finell | A47K 11/06 4/483 |
| 2007/0072214 A1 | 3/2007 | Garvin | |

(Continued)

FOREIGN PATENT DOCUMENTS

| | | |
|---|---|---|
| EP | 0032782 | 7/1981 |
| EP | 0308227 | 3/1989 |
| EP | 0817968 | 1/1998 |
| EP | 1366715 | 12/2003 |
| FR | 2919065 | 1/2009 |

(Continued)

OTHER PUBLICATIONS

Kutzner et al., "Non-invasive detection of colorectal tumors by the combined application of molecular diagnostics and the faecal occult blood test, Cancer Letters", 229 (2005), pp. 33-41. (Year: 2005).*
Kim et al., "Noninvasive molecular biomarkers for the detection of colorectal cancer", BMB reports, vol. 41, Issue 10, pp. 685-692, Sep. 2008.*

(Continued)

*Primary Examiner* — Ethan C Whisenant
(74) *Attorney, Agent, or Firm* — Casimir Jones, S.C.; Mary Ann D. Brow

(57) ABSTRACT

A method of processing a fecal sample from a human subject comprising removing a portion of a collected fecal sample and adding the removed portion of the sample to a buffer that prevents denaturation or degradation of blood proteins found in the sample, and detecting the presence of human blood in the removed portion of the fecal sample. The method further comprises stabilizing the remaining portion of the fecal sample.

14 Claims, No Drawings

Specification includes a Sequence Listing.

(56) References Cited

U.S. PATENT DOCUMENTS

| | | | |
|---|---|---|---|
| 2008/0097238 A1* | 4/2008 | Loktionov | A61B 10/0096 600/562 |
| 2008/0124714 A1* | 5/2008 | Shuber | C12Q 1/6806 435/6.16 |
| 2008/0221056 A1 | 9/2008 | Bayun et al. | |
| 2008/0227208 A1* | 9/2008 | Yee | G01N 33/72 436/66 |
| 2009/0004058 A1* | 1/2009 | Liang | B01L 3/502 422/68.1 |
| 2010/0136572 A1 | 6/2010 | Ataman-Onal et al. | |
| 2012/0164238 A1 | 6/2012 | Joost | |
| 2016/0194723 A1 | 7/2016 | Joost | |

FOREIGN PATENT DOCUMENTS

| | | | |
|---|---|---|---|
| WO | WO 1990/06995 | 6/1990 | |
| WO | WO 1997/46705 | 12/1997 | |
| WO | WO 2000/050640 | 8/2000 | |
| WO | WO 2004/067726 | 8/2004 | |
| WO | WO-2004083399 A2 * | 9/2004 | C12Q 1/6886 |
| WO | WO 2004/0927209 | 10/2004 | |
| WO | WO 2005/014154 | 2/2005 | |
| WO | WO 2005/017207 | 2/2005 | |
| WO | WO 2006/113671 | 10/2006 | |
| WO | WO 2008/010975 | 1/2008 | |
| WO | WO 2008/084219 | 7/2008 | |
| WO | WO-2008084219 A1 * | 7/2008 | A61P 35/04 |
| WO | WO 2008/100913 | 8/2008 | |
| WO | WO 2008/102002 | 8/2008 | |

OTHER PUBLICATIONS

Kutzner et al., "Non-invasive detection of colorectal tumors by the combined application of molecular diagnostics and the faecal occult blood test, Cancer Letters" 229 (2005) 33-41. (Year: 2005).*

Kim et al., BMB reports, vol. 41, Issue 10, pp. 685-692, Sep. 2008. (Year: 2008).*

Abbaszadegan et al., Stool-based DNA testing, a new noninvasive method for colorectal cancer screening, the first report from Iran. World J Gastroenterol. Mar. 14, 2007;13(10):1528-33.

Ahlquist et al., Cologuard Primed to Change Landscape of CRC Screenin, Mayo Clinic Clinical Updates, http://www.mayoclinic.org/medical-professionals/clinical-updates/digestivediseases/cologuard-primed-to-change-landscape-of-crc-screening, pp. 1-4, Dec. 3, 2014.

Auerkari, Methylation of tumor suppressor genes p16(INK4a), p27(Kip1) and E-cadherin in carcinogenesis. Oral Oncol. Jan. 2006;42(1):5-13.

Chen et al., Detection in fecal DNA of colon cancer-specific methylation of the nonexpressed vimentin gene. J Natl Cancer Inst. Aug. 3, 2005;97(15):1124-32.

Conroy et al., Exact Sciences Completes 40,000 Cologuard Tests During First Quarter 2016, Exact Sciences Latest News, pp. 1-10, May 3, 2016.

Exact Sciences, Cologuard(TM) sDNA-based Colorectal Cancer Screening Test—Instructions for Use, pp. 1-71, 2013.

Hammer, Human hybirds. Sci Am. May 2013;308(5):66-71.

Itzkowitz et al., A simplified, noninvasive stool DNA test for colorectal cancer detection. Am J Gastroenterol. Nov. 2008;103(11):2862-70.

Karl et al., Improved diagnosis of colorectal cancer using a combination of fecal occult blood and novel fecal protein markers. Clin Gastroenterol Hepatol. Oct. 2008;6(10):1122-8.

Laird, The power and the promise of DNA methylation markers. Nat Rev Cancer. Apr. 2003;3(4):253-66.

Lenhard et al., Analysis of promoter methylation in stool: a novel method for the detection of colorectal cancer. Clin Gastroenterol Hepatol. Feb. 2005;3(2):142-9.

Levi et al., A quantitative immunochemical faecal occult blood test is more efficient for detecting significant colorectal neoplasia than a sensitive guaiac test. Aliment Pharmacol Ther. May 1, 2006;23(9):1359-64.

Mulder et al., Tumor pyruvate kinase isoenzyme type M2 and immunochemical fecal occult blood test: performance in screening for colorectal cancer. Eur J Gastroenterol Hepatol. Oct. 2007;19(10):878-82.

Rein et al., Identifying 5-methylcytosine and related modifications in DNA genomes. Nucleic Acids Res. May 15, 1998;26(10):2255-64.

Shastri et al., Comparison of an established simple office-based immunological FOBT with fecal tumor pyruvate kinase type M2 (M2-PK) for colorectal cancer screening: prospective multicenter study. Am J Gastroenterol. Jun. 2008;103(6):1496-504.

Sommer et al., Minimal homology requirements for PCR primers. Nucleic Acids Res. Aug. 25, 1989;17(16):6749.

Villar-Garea et al., DNA demethylating agents and chromatin-remodelling drugs: which, how and why? Curr Drug Metab. Feb. 2003;4(1):11-31.

Kim et al., Noninvasive Molecular Biomarkers for the Detection of Colorectal Cancer. BMB Rep. Oct. 31, 2008;41(10):685-92.

Turgeon et al., Fecal DNA-Based Detection of Colorectal Neoplasia. Curr Colorectal Cancer Rep. Oct. 2007;3(4):171-177.

Ahlquist et al., Stool DNA and Occult Blood Testing for Screen Detection of Colorectal Neoplasia. Ann Intern Med. Oct. 7, 2008;149(7):441-W81.

Hoepffner et al., Comparative evaluation of a new bedside faecal occult blood test in a prospective multicentre study. Aliment Pharmacol Ther. Jan. 1, 2006;23(1): 145-54.

Leung et al., Detection of Hypermethylated DNA or Cyclooxygenase-2 Messenger RNA in Fecal Samples of Patients with Colorectal Cancer or Polyps. Am J Gastroenterol 2007;102:1070-6.

Ohlsson et al., Biomarker selection for detection of occult tumour cells in lymph nodes of colorectal cancer patients using real-time quantitative RT-PCR. Br J Cancer. Jul. 1, 20067;95(2):218-25.

Olson et al., DNA Stabilization is Critical for Maximizing Performance of Fecal DNA- Based Colorectal Cancer Tests. Diagn Mol Pathol 2005;14:183-191.

Request for Ex Parte Reexamination of U.S. Pat. No. 11,634,781, filed May 22, 2023, 286 pages.

Declaration of Mr. Anthony P. Shuber, MS, Reexam U.S. Appl. No. 90/015,237, filed May 22, 2023, 63 pages.

* cited by examiner

FECAL SAMPLE PROCESSING AND ANALYSIS COMPRISING DETECTION OF BLOOD

CROSS-REFERENCE TO RELATED APPLICATIONS

This application is a continuation of U.S. application Ser. No. 15/010,436, filed Jan. 29, 2016, which is a continuation of U.S. application Ser. No. 13/147,570, filed Mar. 12, 2012, which is the U.S. national stage of International Application PCT/GB2010/000180, filed Feb. 3, 2010, which claims priority to U.S. Provisional Application No. 61/149,581, filed Feb. 3, 2009. The contents of these applications are incorporated herein by reference in their entireties.

FIELD OF THE INVENTION

The present invention relates to methods and kits for analysis of fecal samples comprising removing a portion of a collected fecal sample and adding the removed portion of the fecal sample to a buffer that prevents denaturation or degradation of blood proteins found in the sample, and comprising detection of blood in the removed portion of the fecal sample, e.g., by immunoassay.

BACKGROUND OF THE INVENTION

Colorectal cancer (CRC) is a leading cause of cancer-related deaths worldwide, and is the second leading cause of cancer-related deaths in the United States. A patient's prognosis is good if the cancer is caught early, when the site of the cancer is confined to its site of origin. However, the cure rates fall once the cancer has spread. Most colon cancers arise from conventional adenomatous polyps (conventional adenoma-to-carcinoma sequence), while some colon cancers appear to arise from the recently recognized serrated adenomatous polyp (serrated adenoma-to-carcinoma theory). Because conventional adenomas and serrated adenomas are usually asymptomatic, mass screening of asymptomatic patients has become the cornerstone for detecting and eliminating these precursor lesions to reduce the risk of colon cancer.

A number of different screening methods for CRC are available. Procedures such as digital rectal examination (DRE); colonoscopy or sigmoidoscopy are highly invasive, painful and can cause a great deal of patient discomfort. Other less invasive screening tests include fecal occult blood test (FOBT); fecal immunochemical test (FIT); barium enema with air contrast; virtual colonoscopy; biopsy (e.g., CT guided needle biopsy); and imaging techniques (e.g., ultrasound, CT scan, PET scan, and MRI).

Colonoscopy has become the primary screening test for CRC because of its high sensitivity and specificity, and the ability to perform polypectomy. While sensitive and specific, the procedure is invasive, costly, has limited availability and includes certain risks such as induction of infection and perforation of the bowel.

A commonly used and less expensive way of screening for CRC is a fecal occult blood test (FOBT), which tests for the presence of blood in faeces. The presence of haemoglobin as a representative blood protein in faeces is an indicator of intestinal bleeding, which is frequently associated with CRC. However, since occult in a fecal sample could be indicative of a variety of gastrointestinal disorders, further medical testing such as colonoscopy remains necessary to identify colorectal cancer.

Fecal occult blood tests fall primarily into two categories, tests based on the use of chromogenic chemical reagents such as gum guaiac and immunochemical tests. The chemically based guaiac methods determine the presence of occult blood by the detection of the peroxidase activity of the hemoglobin in the blood present in the faecal sample. They require catalysis of peroxide into oxygen and water, and the subsequent oxidation of a colorless dye (most often into a colored form). However, peroxidase activity is also found in meats and vegetables. In order to produce accurate results, these tests require restriction of the intake of certain foods, drugs, vitamins, and other substances prior to and during the sample collection period. The sensitivity of the most commonly used guaiac FOBT (Hemoccult) is approximately 50%. Despite a specificity of 98%, the positive predictive value for FOBT is low. Methods of detecting occult blood based on porphyrin (heme and protpoporphyrin IX) analysis or immunologic tests using anti-hemoglobin antibodies improve on these results. Immunochemical tests (FIT or iFOBT) that use anti-hemoglobin antibodies specific for human blood in extracts from stool do not require dietary restrictions; however, they are more complicated and more expensive than peroxidase-based tests. In addition, human hemoglobin in fecal samples degrades with time, resulting in a loss of antigenicity which can produce false negative results. Reported sensitivity of these immunologic tests varies widely but is typically 60-80% depending on the population tested. Specificity is estimated to be ~98%. Because of the intermittent nature of colorectal bleeding, the sensitivity of FOBT and FIT is directly proportional to the number of samples taken and the frequency of testing.

Recent developments in testing look specifically for mutations in DNA characteristic of colorectal neoplasia that are detectable in exfoliated epithelial cells in the stool (Pignone, et al., 2002; Ahlquist, et al., 2002). While neoplastic bleeding is intermittent, epithelial shedding is continual, potentially making stool-based DNA testing (i.e., also known as fecal DNA [f-DNA] and stool DNA [sDNA]) testing more sensitive than other methods. Early studies of molecular feacal screening primarily focused on single mutations. Gene mutations in P53, K-ras, and BAT 26, for instance, have been linked to colorectal cancer and remain detectable in feacal samples. Colorectal neoplasms are varied in nature and no single mutation has been identified as being expressed universally. For this reason, multiple target assay panels (MTAP) are preferably used. PreGen-Plus™ (EX-ACT Sciences Corporation, Maynard, Mass.; Laboratory Corporation of America, Burlington, N.C.) is a single test that identifies the presence of 23 different microsatellite (MSI) mutations known to be associated with CRC, including mutations in BAT-26. Additionally, 21 other point mutations in other genes associated with CRC are included in this test: APC, K-ras, and p53. This test is further designed to detect long DNA fragments, which have been specifically associated with cells called non-apoptotic colonocytes, which are common in CRC. While this test is more sensitive than fecal occult blood testing, it is not as sensitive as colonoscopy and will miss about half of cancers in an average risk group of people without symptoms.

Increased DNA methylation is an epigenetic alteration that is common in human cancers and is often associated with transcriptional silencing. Aberrantly methylated DNA has also been proposed as a potential tumor marker for CRC detection. Genes such as vimentin, which are transcriptionally silent in normal epithelium, have been considered as targets for cancer-associated aberrant methylation and for use as cancer markers (JNCI Journal of the National Cancer Institute 2005 97(15):1124-1132). A combined assay utilizing hypermethylated vimentin gene (hV) and a two site DNA integrity assay (DY), demonstrated a sensitivity of 88% for CRC with a specificity of 82% (Am J Gastroenterol. 2008 November; 103(11):2862-70). Further, ColoSure® is a single marker laboratory developed, stool based DNA test. This method examines DNA in exfoliated colon cells for cancer-associated aberrant methylation of the vimentin gene and reaches a sensitivity range of 72-77% and a specificity range of 83-94% in average risk individuals.

Protein tests provide an alternative method for detecting CRC. Tests assessing the presence of tumor-derived enzymes such as M2 pyruvate kinase (M2-PK), and/or proteins such as calprotectin, carcinoembryonic antigen (CEA), tissue inhibitor of metalloproteinase-1 (TIMP-1) and 5100 calcium binding protein A12 (S100A12) have been described. A diagnosis of colorectal cancer using a combination of fecal occult blood and novel fecal protein markers S100A12 and TIMP-1 has been described in Clin Gastroenterol Hepatol. 2008 October; 6(10):1122-8. Dimeric isoenzyme of pyruvate kinase, M2-PK, expressed by tumor cells, has as well been proposed as a screening tool for CRC. The performance of fecal M2-PK has been evaluated with IFOBT and colonoscopy in Am J Gastroenterol. 2008 June; 103(6):1496-504. Compared to immunochemical FOBTs, TuM2-PK does not have supplemental value for screening for CRC because of a lower sensitivity and specificity (Eur J Gastroenterol Hepatol. 2007 October; 19(10):878-82)

Although combined assays for detecting CRC have been described, their approach targets either multiple protein markers or either multiple DNA alterations. To date, immunochemical tests and DNA tests for CRC detection have been evaluated and compared on a separate basis only.

EP0308227 describes a chemical fecal occult blood test employing a guaiac matrix.

EP0032782 describes a method for the detection of haemoglobin or decomposition products of haemoglobin in feces by means of an immunological reaction by using an antibody specific for human haemoglobin.

U.S. Pat. No. 7,288,413 describes methods that combine a chemical fecal occult blood test and an immunochemical fecal occult blood test.

WO 04/092709 concerns a fecal blood test involving the dispersement of a dye in toilet water.

EP0817968 describes several suitable stool collecting and testing methods and devices.

WO 05/017207 discloses that the vimentin gene can be a common target for methylation and epigenetic gene silencing in colon neoplasia, and may function as a candidate tumor suppressor gene.

WO 2008/084219 relates to detection of colorectal cancer based upon determining methylation of a number of different genes, including panels of genes.

WO 2006/113671 and WO 2008/010975 describe methylation markers relevant to colorectal cancer.

SUMMARY OF THE INVENTION

The invention provides a method of detecting a predisposition to, or the incidence of, colorectal cancer in a faecal sample comprising:

(a) detecting the presence of blood in the faecal sample, wherein detection of the presence of blood is indicative of a predisposition to, or the incidence of, colorectal cancer, (b) detecting an epigenetic modification in the DNA contained within the faecal sample, wherein detection of the epigenetic modification is indicative of a predisposition to, or the incidence of, colorectal cancer and based upon a positive result obtained in either (a) or (b) or in both (a) and (b) detecting a predisposition to, or the incidence of, colorectal cancer.

Also described herein is a method of sample processing, prior to carrying out a method of the invention, comprising removing a portion of a collected faecal sample and adding the removed portion of the sample to a buffer which prevents denaturation or degradation of blood proteins found in the sample.

The invention also provides a method of detecting a predisposition to, or the incidence of, colorectal cancer in a sample comprising detecting an epigenetic modification in a panel of at least two genes selected from PHACTR3, NDRG4 and FOXE1, wherein detection of the epigenetic modification in at least one of the genes in the panel is indicative of a predisposition to, or the incidence of, colorectal cancer.

The invention also provides a method of detecting a predisposition to, or the incidence of, cancer (and in particular colorectal cancer) in a sample comprising detecting an epigenetic modification in at least one gene selected from LAMA1 and CDO1, wherein detection of the epigenetic modification in the at least one gene is indicative of a predisposition to, or the incidence of, cancer (and in particular colorectal cancer).

The invention also relates to a method of detecting a predisposition to, or the incidence of, colorectal cancer (in particular in a faecal sample) comprising detecting an epigenetic modification in at least one gene selected from GPNMB and MMP2, wherein detection of the epigenetic modification in the at least one gene is indicative of a predisposition to, or the incidence of, colorectal cancer.

In related aspects, the invention provides a method for predicting the likelihood of successful treatment of colorectal cancer with a DNA demethylating agent and/or a DNA methyltransferase inhibitor and/or HDAC inhibitor comprising detecting an epigenetic modification in:

(a) a panel of at least two genes selected from PHACTR3, NDRG4 and FOXE1, (b) at least one gene selected from LAMA1 and CDO1; or (c) at least one gene selected from GPNMB and MMP2 (in a faecal sample) wherein detection of the epigenetic modification in at least one of the genes in the panel or in the at least one gene is indicative that the likelihood of successful treatment is higher than if the epigenetic modification is not detected.

a method for predicting the likelihood of resistance to treatment of colorectal cancer with a DNA demethyiating agent and/or DNA methyltransferase inhibitor and/or HDAC inhibitor comprising detecting an epigenetic modification in (a) a panel of at least two genes selected from PHACTR3, NDRG4 and FOXE1, (b) at least one gene selected from LAMA1 and CDO1; or (c) at least one gene selected from GPNMB and MMP2 (in a faecal sample) wherein detection of the epigenetic modification in at least one of the genes in the panel or in the at least one gene is indicative that the likelihood of resistance to treatment is lower than if the epigenetic modification is not detected.

a method of selecting a suitable treatment regimen for colorectal cancer comprising detecting an epigenetic modification in (a) a panel of at least two genes selected from PHACTR3, NDRG4 and FOXE1, (b) at least one gene selected from LAMA1 and CDO1; or (c) at least one gene selected from GPNMB and MMP2 (in a faecal sample) wherein detection of the epigenetic modification in at least one of the genes in the panel or in the at least one gene results in selection of a DNA demethylating agent and/or a DNA methyltransferase inhibitor and/or a HDAC inhibitor for treatment and wherein if the epigenetic modification is not detected, a DNA demethylating agent and/or a DNA methyltransferase inhibitor and/or a HDAC inhibitor is not selected for treatment.

a method for monitoring treatment of colorectal cancer with a DNA demethylating agent and/or a DNA methyltransferase inhibitor and/or HDAC inhibitor comprising detecting an epigenetic modification in (a) a panel of at least two genes selected from PHACTR3, NDRG4 and FOXE 1, (b) at least one gene selected from LAMA1 and CDO1; or (c) at least one gene selected from GPNMB and MMP2 (in a faecal sample) wherein detection of a reduction in the epigenetic modification in at least one of the genes in the panel or in the at least one gene as treatment progresses is indicative of successful treatment.

Thus, the epigenetic modification may be measured at the start of the treatment and then once or more following treatment, or as treatment progresses, in order to determine if the treatment is achieving the desired effect. A return to lower levels of methylation of the genes is considered indicative of effective treatment.

The invention also relates to a kit for detecting a predisposition to, or the incidence of, colorectal cancer in a faecal sample comprising:

(a) means for detecting an epigenetic modification in the DNA contained within the faecal sample, wherein detection of the epigenetic modification is indicative of a predisposition to, or the incidence of, colorectal cancer, and (b) means for detecting the presence of blood in the faecal sample, wherein detection of the presence of blood is indicative of a predisposition to, or the incidence of, colorectal cancer.

Also provided is a kit for any of:

(a) detecting a predisposition to, or the incidence of, colorectal cancer in a sample (b) monitoring treatment of colorectal cancer with a DNA demethylating agent and/or a DNA methyltransferase inhibitor and/or HDAC inhibitor (c) predicting the likelihood of successful treatment of colorectal cancer with a DNA demethylating agent and/or a DNA methyltransferase inhibitor and/or HDAC inhibitor (d) predicting the likelihood of resistance to treatment of colorectal cancer with a DNA demethylating agent and/or DNA methyltransferase inhibitor and/or HDAC inhibitor; or (e) selecting a suitable treatment regimen for colorectal cancer comprising means for detecting an epigenetic modification in a panel of at least two genes selected from PHACTR3, NDRG4 and FOXE1.

Similarly, the invention also provides a kit for any of:

(a) detecting a predisposition to, or the incidence of, colorectal cancer in a sample (b) predicting the likelihood of successful treatment of colorectal cancer with a DNA demethylating agent and/or a DNA methyltransferase inhibitor and/or HDAC inhibitor (c) predicting the likelihood of resistance to treatment of colorectal cancer with a DNA demethylating agent and/or DNA methyltransferase inhibitor and/or HDAC inhibitor; or (d) selecting a suitable treatment regimen for colorectal cancer comprising means for detecting an epigenetic modification in at least one gene selected from LAM A1 and CD01.

The invention also provides a kit for any of:

(a) detecting a predisposition to, or the incidence of, colorectal cancer in a sample (b) predicting the likelihood of successful treatment of colorectal cancer with a DNA demethylating agent and/or a DNA methyltransferase inhibitor and/or HDAC inhibitor (c) predicting the likelihood of resistance to treatment of colorectal cancer with a DNA demethylating agent and/or DNA methyltransferase inhibitor and/or HDAC inhibitor; or (d) selecting a suitable treatment regimen for colorectal cancer comprising means for detecting an epigenetic modification in at least one gene selected from GPNMB and MMP2 and means for processing a faecal sample.

The invention also provides a method of detecting a predisposition to, or the incidence of, colorectal cancer in a faecal sample comprising detecting an epigenetic modification in the DNA contained within the faecal sample, wherein detection of the epigenetic modification is indicative of a predisposition to, or the incidence of, colorectal cancer, characterised in that the faecal sample has previously been stored for at least approximately 6 months, 1, 2, 3, 4, 5, 6 or more years and/or is less than approximately 4, 3, 2, or 1 g in weight.

DETAILED DESCRIPTION OF THE INVENTION

The invention, as set out in the claims, is based upon successful attempts to improve the detection of colorectal cancer. In particular, the invention aims to improve the positive and negative predictive value and also the sensitivity and specificity of detection of colorectal cancer through non-invasive means. The methods of the invention may permit effective detection of colorectal cancer without the requirement for relatively expensive, highly invasive and painful procedures such as digital rectal examination, colonoscopy and sigmoidoscopy to be performed. The invention is based upon a combination of tests for detecting proteins and epigenetic modification markers respectively in the same faecal sample, shown for the first time herein to provide a particularly useful overall test.

Thus, according to a first aspect, the invention provides a method of detecting a predisposition to, or the incidence of, colorectal cancer in a faecal sample comprising, consisting essentially of or consisting of:

(a) detecting the presence of blood in the faecal sample, wherein detection of the presence of blood is indicative of a predisposition to, or the incidence of, colorectal cancer, (b) detecting an epigenetic modification in the DNA contained within the faecal sample, wherein detection of the epigenetic modification is indicative of a predisposition to, or the incidence of, colorectal cancer and based upon a positive result obtained in either (a) or (b) or in both (a) and (b) detecting a predisposition to, or the incidence of, colorectal cancer.

As shown herein, the combination of methylation marker assay and fecal occult blood test (FOBT) gives very specific and sensitive results.

The combined methods of the invention improve the negative predictive value of the existing single tests. By improving sensitivity, the number of false negative results is decreased and this improves negative predictive value.

Step (a) of the methods involves detecting the presence of blood in the faecal sample, wherein detection of the presence of blood is indicative of a predisposition to, or the incidence of, colorectal cancer. Blood in the faeces is an indicator of intestinal bleeding, which is frequently associated with colorectal cancer. Thus, detection of blood in the faecal sample is considered a "positive" result in step (a). Any suitable method for detecting the presence of blood in the sample may be employed. Often, the methods of detecting blood will rely upon detecting a representative blood protein in the faecal sample. In certain embodiments, detecting the presence of blood in the faecal sample comprises, consists essentially of or consists of detection of haemoglobin in the faecal sample. Detection may be through any suitable means, and includes all variants of fecal occult blood tests. The test may be chromogenic or immunological in certain embodiments. The test may rely upon peroxidase activity of hemoglobin. Chromogenic tests are well known and commercially available and may rely upon chemical reagents such as gum guaiac. In specific embodiments, haemoglobin in the faecal sample is detected through immunochemical means. This may involve anti-hemoglobin antibodies in certain embodiments. The term "antibody" or "antibodies" herein refers to an antibody or antibodies, or a derivative thereof that retains specific binding activity. By specific binding activity is meant the ability to specifically bind to hemoglobin. Thus, such a reagent does not bind, or does not bind to a significant degree, to unrelated proteins found in the faecal sample. Any antibody or derivative may be employed. Thus, the antibody may be a monoclonal or polyclonal antibody. The derivative of the antibody that retains specific binding activity may comprise, consist essentially of or consist of a humanized version of a non-human antibody, a heavy chain antibody, a single domain antibody, a nanobody, a Fab fragment or scFv etc. in certain embodiments. Numerous techniques are available for producing antibodies and their derivatized forms, as would be well known to one skilled in the art.

As mentioned above, the combination of techniques maximises sensitivity of detection, without significantly compromising specificity. Thus, the threshold detection concentrations for detection of blood/hemoglobin in step (a) may be those typically employed in fecal occult blood tests. Adding in the step (b) test improves overall sensitivity by picking up additional positive samples. For example, in some embodiments, the result in step (a) is considered positive if the concentration of hemoglobin detected is more than between (about) 50 to (about) 150 ng/ml. In more specific embodiments, the result in step (a) is considered positive if the concentration of hemoglobin detected is more than (about) 100 ng/ml.

However, in other embodiments, the methods of the invention may be employed to improve the sensitivity of the step (a) method, whilst preventing a resultant loss in specificity. By lowering the threshold concentration of blood to be detected in the faecal sample to give a positive result in step (a), the sensitivity of the step (a) method is increased. In order to retain specificity, the step (b) method is employed on those samples in which low levels, that is to say lower than the typically used threshold, of blood were detected in step (a). A positive result from the step (b) method is required to confirm the positive result in step (a) for the "low level" samples. For those samples having blood (especially hemaglobin) concentrations above the typically employed threshold in step (a), it is not necessary to perform the method of step (b), since for these samples the step (a) method is sufficiently specific for this not to be necessary. This has the advantage that the step (b) test is not required for all samples, thus reducing costs and increasing throughput. Thus, in certain embodiments, the result in step (a) is considered positive if the concentration of hemoglobin detected is lower than is typically employed as the threshold concentration of hemoglobin in hemoglobin detection tests, but for those samples in which a "lower than typical threshold" concentration of hemoglobin is detected, step (b) is performed on these samples. The detection of the epigenetic modification in step (b) is then used to confirm the positive result in step (a). The step (b) test is not employed for those samples in which the concentration of hemoglobin detected is higher than the threshold typically employed in hemoglobin detection tests.

In specific embodiments, the result in step (a) is considered positive if the concentration of hemoglobin detected is more than or at least (about) 5 to (about) 50 ng/ml, more specifically more than or at least (about) 5 to (about) 20 ng/ml and more particularly more than or at least (about) 10 ng/ml. By lowering the threshold, the sensitivity of the test is increased. In such embodiments, step (b) is performed only in the event that the concentration of hemoglobin detected is between (about) 5 ng/ml and (about) 250 ng/ml, more specifically between (about) 10 ng/ml and (about) 200 ng/ml. The detection of the epigenetic modification in step (b) is then used to confirm the positive result in step (a). Thus, a positive result in step (b) confirms the result in step (a) as positive. If no epigenetic modification of the DNA is detected, the result of step (a) is considered negative. For samples in which the concentration of hemoglobin detected is more than or at least (about) 200 ng/ml (or (about) 250 ng/ml), it is not necessary to perform step (b), since the result in step (a) will be of high specificity (i.e. is unlikely to be a false positive).

Step (b) involves detecting an epigenetic modification in the DNA contained within the faecal sample, wherein detection of the epigenetic modification is indicative of a predisposition to, or the incidence of, colorectal cancer. Thus, detection of the epigenetic modification is considered a "positive" result in step (b).

In some embodiments, the epigenetic modification is detected in at least one gene selected from PHACTR3, NDRG4, FOXE1, GATA4, GPNMB, TFPI2, SOX17, SYNE1, LAMA1, MMP2, OSMR, SFRP2 and CDO1, with detection of the epigenetic modification in at least one of the genes providing an indication of a predisposition to, or incidence of, colorectal cancer.

In certain embodiments, the epigenetic modification is detected in at least one gene selected from PHACTR3, NDRG4 and FOXE1, with detection of the epigenetic modification in at least one of the genes providing an indication of a predisposition to, or incidence of, colorectal cancer.

PHACTR3 is the gene symbol approved by the HUGO Gene Nomenclature Committee. The gene is located on chromosome 20 (location 20q13.32-q13.33) and the gene sequence is listed under the accession numbers AJ311122 and NM 080672. The gene encodes the phosphatase and actin regulator 3.

NDRG4 is the gene symbol approved by the HUGO Gene Nomenclature Committee. The gene is located on chromosome 16 (location q21-q22.3) and the gene sequence is listed under the accession number AB044947. The gene encodes NDRG family member 4.

FOXE1 is the gene symbol approved by the HUGO Gene Nomenclature Committee. The gene is located on chromosome 9 (location 9q22) and the gene sequence is listed under the accession number U89995. The gene encodes the forkhead box E1 (thyroid transcription factor 2).

GATA4 is the gene symbol approved by the HUGO Gene Nomenclature Committee. The gene is located on chromosome 8 (location 8p23.1-p22) and the gene sequence is listed under the accession numbers AK097060 and NMJ302052. The gene encodes the GATA binding protein 4.

GPNMB is the gene symbol approved by the HUGO Gene Nomenclature Committee. The gene is located on chromosome 7 (location 7p) and the gene sequence is listed under the accession numbers X76534 and NMJ301005340. The gene encodes the glycoprotein (transmembrane) nmb.

TFPI2 is the gene symbol approved by the HUGO Gene Nomenclature Committee. The gene is located on chromosome 7 (location 7q) and the gene sequence is listed under the accession numbers L27624 and NM 006528. The gene encodes tissue factor pathway inhibitor 2.

SOX17 is the gene symbol approved by the HUGO Gene Nomenclature Committee. The gene is located on chromosome 8 (location 8q11.23) and the gene sequence is listed under the accession number AB073988. The gene encodes SRY (sex determining region Y)-box 17.

SYNE1 is the gene symbol approved by the HUGO Gene Nomenclature Committee. The gene is located on chromosome 6 (location 6q24.2-q25.3) and the gene sequence is listed under the accession number AB018339. The gene encodes spectrin repeat containing, nuclear envelope 1.

LAMA1 is the gene symbol approved by the HUGO Gene Nomenclature Committee. The gene is located on chromosome 18 (location 18p11.3) and the gene sequence is listed under the accession numbers X58531 and NM 005559. The gene encodes laminin, alpha 1.

MMP2 is the gene symbol approved by the HUGO Gene Nomenclature Committee. The gene is located on chromosome 16 (location 16q13-q21) and the gene sequence is listed under the accession number NM_001127891. The gene encodes matrix metallopeptidase 2 (gelatinase A, 72 kDa gelatinase, 72 kDa type IV collagenase).

OSMR is the gene symbol approved by the HUGO Gene Nomenclature Committee. The gene is located on chromosome 5 (location 5p13.2) and the gene sequence is listed under the accession number U60805 and NM 003999. The gene encodes the oncostatin M receptor.

SFRP2 is the gene symbol approved by the HUGO Gene Nomenclature Committee. The gene is located on chromosome 4 (location 4q31.3) and the gene sequence is listed under the accession number AF017986. The gene encodes the secreted frizzled-related protein 2.

CDO1 is the gene symbol approved by the HUGO Gene Nomenclature Committee. The gene is located on chromosome 5 (location 5q23.2) and the gene sequence is listed under the accession number NM_001801. The gene encodes the cysteine dioxygenase, type I.

By "gene" is meant the specific known gene in question. It may also relate to any gene which is taken from the family to which the named "gene" belongs, in certain circumstances, and includes according to all aspects of the invention not only the particular sequences found in the publicly available database entries, but also encompasses transcript and nucleotide variants of these sequences, with the proviso that methylation or another epigenetic modification of the gene is linked to the incidence of colorectal cancer. Variant sequences may have at least 90%, at least 91%, at least 92%, at least 93%, at least 94%, at least 95%, at least 96%, at least 97%, at least 98%, or at least 99% nucleotide sequence identity with the nucleotide sequences in the database entries. Computer programs for determining percentage nucleotide sequence identity are available in the art, including the Basic Local Alignment Search Tool (BLAST) available from the National Center for Biotechnology Information.

The methods of the invention are generally in vitro methods carried out on an isolated test sample. The methods are used to diagnose colorectal cancer. In certain embodiments the methods may also include the step of obtaining the sample. The test sample is generally from a human subject. The subject may be suspected of being tumorigenic. More specifically the subject may be suspected of suffering from a colorectal cancer.

In specific embodiments of the methods, the epigenetic modification is detected in a panel of at least two genes selected from PHACTR3, NDRG4 and FOXE1, with detection of the epigenetic modification in at least one of the genes providing an indication of a predisposition to, or incidence of, colorectal cancer. Specific panels which may be employed comprise, consist essentially of or consist of PHACTR3, NDRG4 and FOXE1, NDRG4 and FOXE1, PHACTR3 and NDRG4, or PHACTR3 and FOXE1.

In other embodiments, the epigenetic modification is detected in at least one gene selected from LAMA1 and CDO1. In further embodiments, the epigenetic modification is detected in at least one gene selected from GPNMB and MMP2 The methods of the invention may have diagnostic and prognostic value, and this is included within the definition of the term "detecting a predisposition to, or incidence of, colorectal cancer". The prognostic value of the methods of the invention may be used as a marker of potential susceptibility to colorectal cancer or as a marker for progression from adenoma to cancer for example. Thus patients at risk may be identified before the disease has a chance to manifest itself in terms of symptoms identifiable in the patient. Initial detection as well as follow-up detection, for example following treatment, is also included within the definition. Follow up detection may be performed after any treatment. Examples include following polypectomy (removal of polyps) and following surgery to remove a colorectal carcinoma, severe neoplasia or advanced adenoma.

The methods of the invention may be carried out on purified or unpurified DNA-containing samples. However, in specific embodiments, DNA is isolated/extracted/purified from the sample. Any suitable DNA isolation technique may be utilised. Examples of purification techniques may be found in standard texts such as Molecular Cloning—A Laboratory Manual (Third Edition), Sambrook and Russell (see in particular Appendix 8 and Chapter 5 therein). In some embodiments, purification involves alcohol precipitation of DNA. Preferred alcohols include ethanol and isopropanol. Suitable purification techniques also include salt-based precipitation methods. Thus, in specific embodiments the DNA purification technique comprises use of a high concentration of salt to precipitate contaminants. The salt may comprise, consist essentially of or consist of potassium acetate and/or ammonium acetate for example. The method may further include steps of removal of contaminants which have been precipitated, followed by recovery of DNA through alcohol precipitation.

In alternative embodiments, the DNA purification technique is based upon use of organic solvents to extract contaminants from cell lysates. Thus, in certain embodiments, the method comprises use of phenol, chloroform and isoamyl alcohol to extract the DNA. Suitable conditions are employed to ensure that the contaminants are separated into the organic phase and that DNA remains in the aqueous phase.

In specific embodiments of these purification techniques, extracted DNA is recovered through alcohol precipitation, such as ethanol or isopropanol precipitation.

Amplification of DNA (using PCR) from natural sources is often inhibited by co-purified contaminants and various methods adopted for DNA extraction from environmental samples are available and provide an alternative for isolating DNA from faecal samples, according to specific embodiments of the invention. For instance, the QIAamp DNA Stool Mini Kit from QIAGEN adsorbs DNA-damaging substances and PCR inhibitors present in the sample by InhibitEX. Other examples for application to faecal samples include the Wizard Genomic DNA Purification Kit (Promega), the NucliSENS® easyMAG™ (Biomerieux) and nucleic acid purification kits manufactured by Macherey Nagel.

The methods of the invention may also, as appropriate, incorporate quantification of isolated/extracted/purified DNA in the sample. Quantification of the DNA in the sample may be achieved using any suitable means. Quantitation of nucleic acids may, for example, be based upon use of a spectrophotometer, a fluorometer or a UV transilluminator. Examples of suitable techniques are described in standard texts such as Molecular Cloning—A Laboratory Manual (Third Edition), Sambrook and Russell (see in particular Appendix 8 therein). In some embodiments, kits such as the Picogreen® dsDNA quantitation kit available from Molecular Probes, Invitrogen may be employed to quantify the DNA.

The inventor has determined that faecal samples for use in the invention do not necessarily have to be freshly collected. This applies in particular for performing step (b) and thus also the further methods of the invention discussed herein where epigenetic modifications in specific genes are determined in faecal samples, Thus, samples collected 1, 2, 3, 4, 5, 6 or more years ago may be employed. The historical samples may have been frozen for storage. Freezing is performed at a suitable temperature, such as 20° C. for example. Lyophilisation may be performed in certain embodiments to permit storage of the faecal samples. The sample may be frozen without the addition of a stabilizing buffer in certain embodiments as it has been shown that this is not necessary, when the sample is frozen, in order to retain DNA integrity in the sample. In other embodiments, a suitable stabilizing buffer as known to those in the art, may be added to the sample before and/or after storage.

The inventor has also discovered that a minimal stool sample, including a minimal sample derived from a historical sample as discussed herein, may successfully be employed in the methods of the invention. This is particularly applicable to performing step (b) and thus is also applicable to the further aspects of the invention discussed herein where epigenetic modifications in specific genes are determined, in faecal samples. Thus, only a portion of a collected faecal sample need be employed in the methods of the invention in order to achieve reliable results. Reliable results may be achieved by isolating, extracting or purifying DNA from less than 5 g of faecal sample, in particular from approximately 4, 3, 2, or 1 g of faecal sample. The faecal sample may be present in an appropriate volume of homogenizing buffer to facilitate DNA isolation, extraction and purification.

As discussed above, suitable commercially available kits, such as the QIAamp DNA Stool Mini Kit, may be employed in order to extract the DNA and remove potential inhibitors found in the faecal sample. This may involve processing smaller volumes of the overall faecal sample and pooling the resultant DNA in certain embodiments. For example, volumes of approximately 1 ml or less, such as approximately 750, 500, 250 or 100 μl may be used for DNA extraction. The resultant DNA from 2, 3, 4, 5 or more extractions may be pooled to give an overall DNA sample to be assessed according to the methods of the invention. DNA in the sample, pre- and/or post-pooling can be quantified as required, as discussed herein.

Thus, the invention provides a method of detecting a predisposition to, or the incidence of, colorectal cancer in a faecal sample comprising, consisting essentially of or consisting of detecting an epigenetic modification in the DNA contained within the faecal sample, wherein detection of the epigenetic modification is indicative of a predisposition to, or the incidence of, colorectal cancer, characterised in that the faecal sample has previously been stored for at least approximately 6 months, 1, 2, 3, 4, 5, 6 or more years and/or is less than approximately 4, 3, 2, or 1 g in weight (prior to addition of homogenization buffer).

The detailed discussion of determination of epigenetic modifications provided herein applies mutatis mutandis to this aspect of the invention.

"Colorectal cancer", also called colon cancer or bowel cancer, is defined to include cancerous growths, carcinomas, severe neoplasias and advanced adenomas in the colon, rectum and appendix.

"Epigenetic modification" is defined herein to include any alteration in the DNA, generally resulting in diminished gene expression, which is mediated by mechanisms other than alterations in the primary nucleotide sequence of a gene. Epigenetic modifications may, in certain circumstances be stable heritable traits. A number of related mechanisms that cause alteration in gene expression are recognised and include DNA methylation, histone changes (for example changes in histone acetylation) which may lead to chromatin remodelling and RNA interference. In many cases, hypermethylation of DNA incorrectly switches off critical genes allowing cancers to develop and progress. In specific embodiments, the epigenetic modification is methylation. In particular, aberrant methylation, which may be referred to as hypermethylation, of the gene or genes is detected. Typically, the methylation status is determined in suitable CpG islands which are often found in the promoter region of the gene(s). The term "methylation", "methylation state" or "methylation status" refers to the presence or absence of 5-methylcytosine at one or a plurality of CpG dinucleotides within a DNA sequence. CpG dinucleotides are typically concentrated in the promoter regions and exons of human genes. CpG dinucleotides susceptible to methylation may be found in the promoter region, exons and introns of human genes. Promoter, exon and intron regions can all thus be assessed for methylation. A "promoter" is a region extending typically between approximately 1 Kb, 500 bp or 150 to 300 bp upstream from the transcription start site. In some embodiments, the CpG island surrounding or positioned around the transcription start site is analysed to determine its methylation status. Alternatively, the methylation status of the exon and/or intron regions of may be determined as appropriate. The identification of CpG islands, to assess for determination of methylation status, is a matter of routine for one skilled in the art and various techniques, including in silico techniques, are available.

Since hypermethylation of a gene may result in diminished gene expression it may be possible, in certain embodiments, to carry out the methods of the invention by determining gene expression of the DNA in the faecal sample, rather than investigating the methylation status of the DNA directly. Many suitable techniques are available for determining gene expression at either the RNA or protein level. In certain embodiments, expression at the RNA level is determined by reverse transcriptase polymerase chain reaction (RT-PCR). In alternative embodiments, expression is determined at the protein level. Again, any suitable technique may be employed such as western blotting, ELISA etc.

Measurement of expression of a gene on its own may not necessarily conclusively indicate that the silencing is epigenetic, as the mechanism of silencing could be genetic, for example, by somatic mutation. Accordingly, in certain embodiments, the methods of the invention incorporate an appropriate re-expression assay which is designed to reverse epigenetic silencing. Appropriate treatment of the sample using a demethylating agent, such as a DNA-methyltransferase (DMT) inhibitor may reverse epigenetic silencing of the relevant gene. Suitable reagents include, but are not limited to, DAC (5'-deazacytidine), TSA or any other treatment affecting epigenetic mechanisms present in cell lines. Suitable reagents are discussed herein with respect to the pharmacogenetic, treatment monitoring and treatment aspects of invention, which discussion applies mutatis mutandis. Typically, expression is reactivated or reversed upon treatment with such reagents, indicating that the silencing is epigenetic.

Determination of the methylation status may be achieved through any suitable means. Suitable examples include bisulphite genomic sequencing and/or by methylation specific PCR. Various techniques for assessing methylation status are known in the art and can be used in conjunction with the present invention: sequencing, methylation-specific PCR (MS-PCR), melting curve methylation-specific PCR (McMS-PCR), MLPA with or without bisulphite treatment, QAMA (Zeschnigk et al, 2004), MSRE-PCR (Melnikov et al, 2005), MethyLight (Eads et al., 2000), ConLight-MSP (Rand et al., 2002), bisulphite conversion-specific methylation-specific PCR (BS-MSP)(Sasaki et al., 2003), COBRA (which relies upon use of restriction enzymes to reveal methylation dependent sequence differences in PCR products of sodium bisulphite—treated DNA), methylation-sensitive single-nucleotide primer extension conformation(MS-SNuPE), methylation-sensitive single-strand conformation analysis (MS-SSCA), Melting curve combined bisulphite restriction analysis (McCOBRA)(Akey et al., 2002), PyroMethA, HeavyMethyl (Cottrell et al. 2004), MALDI-TOF, MassARRAY, Quantitative analysis of methylated alleles (QAMA), enzymatic regional methylation assay (ERMA)1 QBSUPT, MethylQuant, Quantitative PCR sequencing and oligonucleotide-based microarray systems, Pyrosequencing, Meth-DOP-PCR. A review of some useful techniques for DNA methylation analysis is provided in Nucleic acids research, 1998, Vol. 26, No. 10, 2255-2264, Nature Reviews, 2003, Vol. 3, 253-266; Oral Oncology, 2006, Vol. 42, 5-13, which references are incorporated herein in their entirety.

Techniques for assessing methylation status are based on distinct approaches. Some include use of endonucleases. Such endonucleases may either preferentially cleave methylated recognition sites relative to non-methylated recognition sites or preferentially cleave non-methylated relative to methylated recognition sites. Some examples of the former are Ace III, Ban I, BstN I, Msp I, and Xma I. Examples of the latter are Ace II, Ava I, BssH II, BstU I, Hpa II, and Not I. Differences in cleavage pattern are indicative for the presence or absence of a methylated CpG dinucleotide. Cleavage patterns can be detected directly, or after a further reaction which creates products which are easily distinguishable. Means which detect altered size and/or charge can be used to detect modified products, including but not limited to electrophoresis, chromatography, and mass spectrometry.

Alternatively, the identification of methylated CpG dinucleotides may utilize the ability of the methyl binding domain (MBD) of the MeCP2 protein to selectively bind to methylated DNA sequences (Cross et al, 1994; Shiraishi et al, 1999). The MBD may also be obtained from MBP, MBP2, MBP4, poly-MBD (Jorgensen et al., 2006) or from reagents such as antibodies binding to methylated nucleic acid. The MBD may be immobilized to a solid matrix and used for preparative column chromatography to isolate highly methylated DNA sequences. Variant forms such as expressed His-tagged methyl-CpG binding domain may be used to selectively bind to methylated DNA sequences. Eventually, restriction endonuclease digested genomic DNA is contacted with expressed His-tagged methyl-CpG binding domain. Other methods are well known in the art and include amongst others methylated-CpG island recovery assay (MIRA). Another method, MB-PCR, uses a recombinant, bivalent methyl-CpG-binding polypeptide immobilized on the walls of a PCR vessel to capture methylated DNA and the subsequent detection of bound methylated DNA by PCR.

Further approaches for detecting methylated CpG dinucleotide motifs use chemical reagents that selectively modify either the methylated or non-methylated form of CpG dinucleotide motifs. Suitable chemical reagents include hydrazine and bisulphite ions. The methods of the invention preferably use bisulphite ions. The bisulphite conversion relies on treatment of DNA samples with sodium bisulphite which converts un methylated cytosine to uracil, while methylated cytosines are maintained (Furuichi et al., 1970). This conversion finally results in a change in the sequence of the original DNA. It is general knowledge that the resulting uracil has the base pairing behaviour of thymidine which differs from cytosine base pairing behaviour. This makes the discrimination between methylated and non-methylated cytosines possible. Useful conventional techniques of molecular biology and nucleic acid chemistry for assessing sequence differences are well known in the art and explained in the literature. See, for example, Sambrook, J., et al., Molecular cloning: A laboratory Manual, (2001) 3rd edition, Cold Spring Harbor, N.Y.; Gait, M. J. (ed.), Oligonucleotide Synthesis, A Practical Approach, IRL Press (1984); Hames B. D., and Higgins, S J. (eds.), Nucleic Acid Hybridization, A Practical Approach, IRL Press (1985); and the series, Methods in Enzymology, Academic Press, Inc.

Some techniques use primers for assessing the methylation status at CpG dinucleotides. Two approaches to primer design are possible. Firstly, primers may be designed that themselves do not cover any potential sites of DNA methylation. Sequence variations at sites of differential methylation are located between the two primers and visualisation of the sequence variation requires further assay steps. Such primers are used in bisulphite genomic sequencing, COBRA, Ms-SnuPE and several other techniques. Secondly, primers may be designed that hybridize specifically with either the methylated or unmethylated version of the initial treated sequence. After hybridization, an amplification reaction can be performed and amplification products assayed using any detection system known in the art. The presence of an amplification product indicates that a sample hybridized to the primer. The specificity of the primer indicates whether the DNA had been modified or not, which in turn indicates whether the DNA had been methylated or not. If there is a sufficient region of complementarity, e.g., 12, 15, 18, or 20 nucleotides, to the target, then the primer may also contain additional nucleotide residues that do not interfere with hybridization but may be useful for other manipulations. Examples of such other residues may be sites for restriction endonuclease cleavage, for ligand binding or for factor binding or linkers or repeats. The oligonucleotide primers may or may not be such that they are specific for modified methylated residues.

A further way to distinguish between modified and unmodified nucleic acid is to use oligonucleotide probes. Such probes may hybridize directly to modified nucleic acid or to further products of modified nucleic acid, such as products obtained by amplification. Probe-based assays exploit the oligonucleotide hybridisation to specific sequences and subsequent detection of the hybrid. There may also be further purification steps before the amplification product is detected e.g. a precipitation step. Oligonucleotide probes may be labelled using any detection system known in the art. These include but are not limited to fluorescent moieties, radioisotope labelled moieties, bioluminescent moieties, luminescent moieties, chemiluminescent moieties, enzymes, substrates, receptors, or ligands.

In the MSP approach, DNA may be amplified using primer pairs designed to distinguish methylated from unmethylated DNA by taking advantage of sequence differences as a result of sodium-bisulphite treatment (Herman et al., 1996; and WO 97/46705). For example, bisulphite ions modify non-methylated cytosine bases, changing them to uracil bases. Uracil bases hybridize to adenine bases under hybridization conditions. Thus an oligonucleotide primer which comprises adenine bases in place of guanine bases would hybridize to the bisulphite-modified DNA, whereas an oligonucleotide primer containing the guanine bases would hybridize to the non-modified (methylated) cytosine residues in the DNA. Amplification using a DNA polymerase and a second primer yield amplification products which can be readily observed, which in turn indicates whether the DNA had been methylated or not Whereas PCR is a preferred amplification method, variants on this basic technique such as nested PCR and multiplex PCR are also included within the scope of the invention.

As mentioned earlier, a preferred embodiment for assessing the methylation status of the relevant gene requires amplification to yield amplification products. The presence of amplification products may be assessed directly using methods well known in the art. They simply may be visualized on a suitable gel, such as an agarose or polyacrylamide gel. Detection may involve the binding of specific dyes, such as ethidium bromide, which intercalate into double-stranded DNA and visualisation of the DNA bands under a UV illuminator for example. Another means for detecting amplification products comprises hybridization with oligonucleotide probes. Alternatively, fluorescence or energy transfer can be measured to determine the presence of the methylated DNA.

A specific example of the MSP technique is designated real-time quantitative MSP (QMSP), and permits reliable quantification of methylated DNA in real time or at end point. Real-time methods are generally based on the continuous optical monitoring of an amplification procedure and utilise fluorescently labelled reagents whose incorporation in a product can be quantified and whose quantification is indicative of copy number of that sequence in the template. One such reagent is a fluorescent dye, called SYBR Green I that preferentially binds double-stranded DNA and whose fluorescence is greatly enhanced by binding of double-stranded DNA. Alternatively, labeled primers and/or labeled probes can be used for quantification. They represent a specific application of the well known and commercially available real-time amplification techniques such as TAQMAN®, MOLECULAR BEACONS®, AMPLIFLUOR® and SCORPION® DzyNA®, Plexor™ etc. In the real-time PCR systems, it is possible to monitor the PCR reaction during the exponential phase where the first significant increase in the amount of PCR product correlates to the initial amount of target template.

In specific embodiments, methylation specific PCR/amplification is utilised. This may be carried out in real time or at end point. The real time or end point PCR/amplification may involve use of hairpin primers (Amplifluor), hairpin probes (Molecular Beacons), hydrolytic probes (Taqman), FRET probe pairs (Lightcycler), primers incorporating a hairpin probe (Scorpion), fluorescent dyes (SYBR Green etc.), primers incorporating the complementary sequence of a DNAzyme and a cleavable fluorescent DNAzyme substrate or oligonucleotide blockers, for example.

Real-Time PCR detects the accumulation of amplicon during the reaction. Real-time methods do not need to be utilised, however. Many applications do not require quantification and Real-Time PCR is used only as a tool to obtain convenient results presentation and storage, and at the same time to avoid post-PCR handling. Thus, analyses can be performed only to confirm whether the target DNA is present in the sample or not. Such end-point verification is carried out after the amplification reaction has finished. This knowledge can be used in a medical diagnostic laboratory to detect a predisposition to, or the incidence of, cancer in a patient. End-point PCR fluorescence detection techniques can use the same approaches as widely used for Real Time PCR. For example, «Gene» detector allows the measurement of fluorescence directly in PCR tubes.

In real-time embodiments, quantitation may be on an absolute basis, or may be relative to a constitutively methylated DNA standard, or may be relative to an unmethylated DNA standard. Methylation status may be determined by using the ratio between the signal of the marker under investigation and the signal of a reference gene where methylation status is known (such as β-actin for example), or by using the ratio between the methylated marker and the sum of the methylated and the non-methylated marker. Alternatively, absolute copy number of the methylated marker gene can be determined.

Suitable controls may need to be incorporated in order to ensure the method chosen is working correctly and reliably. Suitable controls may include assessing the methylation status of a gene known to be methylated. This experiment acts as a positive control to ensure that false negative results are not obtained. The gene may be one which is known to be methylated in the sample under investigation or it may have been artificially methylated, for example by using a suitable methyltransferase enzyme, such as SssI methyltransferase.

Additionally or alternatively, suitable negative controls may be employed with the methods of the invention. Here, suitable controls may include assessing the methylation status of a gene known to be unmethylated or a gene that has been artificially demethylated. This experiment acts as a negative control to ensure that false positive results are not obtained.

Whilst PCR is the preferred nucleic acid amplification technique, other amplification techniques may also be utilised to detect the methylation status of the concerned gene. Such amplification techniques are well known in the art, and include methods such as NASBA (Compton, 1991), 3SR (Fahy et al., 1991) and Transcription Mediated Amplification (TMA). Other suitable amplification methods include the ligase chain reaction (LCR) (Barringer et al, 1990), selective amplification of target polynucleotide sequences (U.S. Pat. No. 6,410,276), consensus sequence primed polymerase chain reaction (U.S. Pat. No. 4,437,975), arbitrarily primed polymerase chain reaction (WO 90/06995), invader technology, strand displacement technology, and nick displacement amplification (WO 2004/067726). This list is not intended to be exhaustive; any nucleic acid amplification technique may be used provided the appropriate nucleic acid product is specifically amplified. Thus, these amplification techniques may be tied in to MSP and/or bisulphite sequencing techniques for example.

In specific embodiments, the methods utilise primers selected from primers comprising, consisting essentially of or consisting of the nucleotide sequences set forth in table 1. Suitable primer pairs can be selected from the primers listed in the table based upon the gene or genes of interest. In specific embodiments, the methods utilise primers selected from primers comprising, consisting essentially of or consisting of the nucleotide sequences set forth as SEQ ID Nos: 1 and 2 (PHACTR3), 4 and 5 (FOXE1), and 7 and 8 (NDRG4) in order to detect methylation status in the DNA. These primers are particularly useful in MSP based methods of detection. Each of the primers covers one or more methylation sites and is specific for the methylated sequence following bisulphite treatment.

In certain embodiments, the methods utilise probes selected from probes comprising, consisting essentially of or consisting of the nucleotide sequences set forth in table 1. Suitable probes can be selected from the probes listed in the table based upon the gene or genes of interest. In specific embodiments, the methods utilise probes selected from probes comprising, consisting essentially of or consisting of the nucleotide sequences set forth as SEQ ID Nos: 3 (PHACTR3), 6 (FOXE1), and 9 (NDRG4) in order to detect methylation status in the DNA. Each of the probes covers one or more methylation sites and is specific for the methylated sequence following bisulphite treatment. The probes may be utilised in combination with the primers listed above in specific embodiments. The probes may be fluorescently labelled, in particular with a donor and an acceptor (or quencher) fluorophore to permit FRET to occur and allow real-time or end-point detection. An example of a donor moiety is FAM and an example of an acceptor or quencher moiety is DABCYL.

The methods of the invention are performed using a faecal sample. In certain embodiments, a single faecal sample is utilised as the source of the sample for (a) and (b). However, the sample may need to be split to permit (a) and (b) to be carried out. Thus the sample may need to be treated to differing degrees in order to permit the separate steps to be carried out. As a result, after obtaining the faecal sample, the sample may be apportioned appropriately to allow the DNA and protein testing to be carried out separately.

In the context of these methods of the invention, there is the requirement for appropriate sample processing, since two separate detection techniques may be performed on a single sample. To meet this requirement, the invention provides a method of sample processing, prior to carrying out a method of the invention (tests (a) and (b)), comprising removing a portion of a collected faecal sample and adding the removed portion of the sample to a buffer which prevents denaturation or degradation of blood proteins found in the sample. The faecal sample may be collected at home by the subject. This may involve defecation into a suitable vessel. From this sample is removed a sufficient portion of the sample. This removed portion is then added to a suitable container, which may already contain a buffer. Alternatively, the buffer may be added with the removed portion of the sample or (shortly) afterwards. The removed portion is thus prepared for performance of step (a), namely detecting the presence of blood in the faecal sample, wherein detection of the presence of blood is indicative of a predisposition to, or the incidence of, colorectal cancer, on this sample. The buffer prevents denaturation or degradation of blood proteins found in the sample. Suitable buffers for protein preservation are known in the art and commercially available. The remaining portion of the sample may remain in the vessel in which it was originally collected, prior to carrying out step (b), namely detecting an epigenetic modification in the DNA contained within the faecal sample, wherein detection of the epigenetic modification is indicative of a predisposition to, or the incidence of, colorectal cancer. Suitable buffers for maintaining DNA integrity may be added to the remaining portion of the sample, in certain embodiments. The separated samples may be suitably labelled to ensure that they are paired up correctly during subsequent processing, including data analysis and comparison.

Following collection of the sample and suitable processing, the method may further comprise forwarding or otherwise delivering the removed portion of the collected faecal sample to a laboratory for performing step (a) of the method, as defined herein, on the removed portion of the collected faecal sample. The forwarding or otherwise delivering may occur within any suitable time frame following sample collection. In certain embodiments, the forwarding or otherwise delivering may occur within 6, 12, 24, 48 or 72 hours of sample collection. The method may then further comprise performing step (a) of the method on the removed portion of the collected faecal sample once it has been delivered. As described herein, step (b) may only be performed on a specific subset of samples in which blood is detected at low levels. Thus, the methods of sample processing may involve sorting those samples with detection of low levels of blood detected in step (a) (as defined herein) for testing in step (b). The appropriate remaining portions of the collected samples in which step (b) is not required (i.e. where a confirmation of the result in step (a) is not required—either because the no blood is detected or the level of blood is above the typically employed threshold (such as 200 ng/ml)) may then be discarded as appropriate.

Similarly, following collection of the sample and suitable processing, the method may further comprise forwarding or otherwise delivering the remaining portion of the collected faecal sample to a laboratory for performing step (b) of the method, as defined herein, on the remaining portion of the collected faecal sample. The forwarding or otherwise delivering may occur within any suitable time frame following sample collection. In certain embodiments, the forwarding or otherwise delivering may occur within 6, 12, 24, 48 or 72 hours of sample collection. The method may then further comprise performing step (b) of the method on the remaining portion of the collected faecal sample once it has been delivered.

In certain embodiments, the forwarding or other delivery of the removed and remaining portions of the collected faecal sample may be carried out to the same location, optionally at the same time. This is the case where the same laboratory is carrying out both steps (a) and (b) which may be the case where the laboratory has the capacity to perform both types of test.

As discussed herein, the faecal samples for use in the invention do not necessarily have to be freshly collected. The discussion above applies mutatis mutandis here. Similarly, a minimal stool sample, including a minimal sample derived from a historical sample as discussed herein, may successfully be employed in the methods of the invention. This is particularly applicable to performing step (b) (i.e. on the remaining portion of the faecal sample). Again, the discussion above applies mutatis mutandis here, including relating to pooling of samples during the DNA extraction process. The requirement for minimal or portioned samples for step (b) may be advantageous by permitting more of the sample to be utilised to perform step (a), potentially improving the sensitivity of step (a).

As shown herein, methylation status determination based upon a panel of at least two genes selected from PHACTR3, NDRG4 and FOXE1 can provide sensitive and specific detection of colorectal cancer. Thus, according to a related aspect, the invention provides a method of detecting a predisposition to, or the incidence of, colorectal cancer in a sample comprising detecting an epigenetic modification in a panel of at least two genes selected from PHACTR3, NDRG4 and FOXE1, wherein detection of the epigenetic modification in at least one of the genes in the panel is indicative of a predisposition to, or the incidence of, colorectal cancer.

It is also shown herein that methylation of LAMA1 and CDO1 is linked to the incidence of colorectal cancer. These genes have not been previously linked to colorectal cancer. Thus, the invention also provides a method of detecting a predisposition to, or the incidence of, cancer (and in particular colorectal cancer) in a sample comprising detecting an epigenetic modification in at least one gene selected from LAMA1 and CDO1, wherein detection of the epigenetic modification in the at least one gene is indicative of a predisposition to, or the incidence of, cancer (and in particular colorectal cancer).

Evidence is also presented herein that methylation of GPNMB and MMP2 is linked to colorectal cancer, in particular based upon faecal samples. Thus, the invention also relates to a method of detecting a predisposition to, or the incidence of, colorectal cancer (in particular in a faecal sample) comprising detecting an epigenetic modification in at least one gene selected from GPNMB and MMP2, wherein detection of the epigenetic modification in the at least one gene is indicative of a predisposition to, or the incidence of, colorectal cancer.

As for the first aspect of the invention, the epigenetic modification is often methylation and thus these methods may involve determining the methylation status of the at least one gene or panel of genes. Thus, aberrant methylation, or "hypermethylation", of the gene(s) may be detected. Various methods for determining methylation status are discussed herein, which discussion applies mutatis mutandis to these aspects of the invention. In specific embodiments, methylation specific PCR/amplification is utilised. This may be carried out in real time or at end point. The real time or end point PCR/amplification may involve use of hairpin primers (Amplifluor), hairpin probes (Molecular Beacons), hydrolytic probes (Taqman), FRET probe pairs (Lightycler), primers incorporating a hairpin probe (Scorpion), fluorescent dyes (SYBR Green etc.), primers incorporating the complementary sequence of a DNAzyme and a cleavable fluorescent DNAzyme substrate or oligonucleotide blockers, for example. The methods may apply suitable primers and probes selected from table 1. In specific embodiments, the methods utilise primers selected from primers comprising, consisting essentially of or consisting of the nucleotide sequences set forth as SEQ ID Nos: 1 and 2 (PHACTR3), 4 and 5 (FOXE1), and 7 and 8 (NDRG4). In further embodiments, the methods utilise probes selected from probes comprising, consisting essentially of or consisting of the nucleotide sequences set forth as SEQ ID Nos: 3 (PHACTR3), 6 (FOXE1), and 9 (NDRG4). In other embodiments, the methods utilise primers selected from primers comprising the nucleotide sequences set forth as SEQ ID Nos: 28 and 29 (LAMA1) and 34 and 35 (CDO1). In further related embodiments, the methods utilise probes selected from probes comprising the nucleotide sequences set forth as SEQ ID Nos: 30 (LAMA1) and 36 (CDO1). In other embodiments, the methods utilise primers selected from primers comprising the nucleotide sequences set forth as SEQ ID Nos: 22 and 23 (GPNMB) and 31 and 32 (MMP2). In related embodiments, the methods utilise probes selected from probes comprising the nucleotide sequences set forth as SEQ ID Nos: 24 (GPNMB) and 33 (MMP2).

These methods of the invention may be ex vivo or in vitro methods carried out on a test sample. The methods may be non-invasive. The methods may be used to identify any stage of colorectal cancer, including pre-malignancies such as adenomas right through to carcinomas (see the definition of colorectal cancer herein).

The "sample" in which the epigenetic modification is detected may comprise, consist essentially of or consist of a tissue sample, a faecal sample or a blood sample. In preferred embodiments, the sample is a faecal sample. Historical samples (such as those collected at least approximately 1 year ago) and small samples (such as those of approximately 1 g) may be useful in the methods of the invention, as discussed herein (which discussion applies mutatis mutandis). In specific embodiments, the tissue sample comprises, consists essentially of or consists of a colon and/or rectum and/or appendix sample. However, the sample may be from any representative tissue sample, body fluid, body fluid precipitate or lavage specimen, as required provided that detection of the epigenetic modification in the sample provides a reliable indicator of colorectal cancer. The sample may be obtained from a human subject. Test samples for diagnostic, prognostic, or personalised medicinal uses can be obtained from surgical samples, such as biopsies or fine needle aspirates, from paraffin embedded tissues, from frozen tumor tissue samples, from fresh tumor tissue samples, from a fresh or frozen body fluid, for example. Non-limiting examples include whole blood, bone marrow, cerebral spinal fluid, peritoneal fluid, pleural fluid, lymph fluid, serum, plasma, urine, chyle, stool, ejaculate, sputum, nipple aspirate, saliva, swabs specimen, wash or lavage fluid and/or brush specimens.

These methods may also include the step of obtaining the test sample, in certain embodiments. The tissue sample or liquid sample comprising the nucleic acid may be lysed or need to be concentrated to create a mixture of biological compounds comprising nucleic acids and other components. Alternatively, the nucleic acid may need to be cleared of proteins or other contaminants, e.g. by treatment with proteinase K. Procedures for lysing or concentrating biological samples are known by the person skilled in the art and can be chemical, enzymatic or physical in nature. A combination of these procedures may be applicable as well. For instance, lysis may be performed using ultrasound, high pressure, shear forces, alkali, detergents or chaotropic saline solutions, or proteases or lipases. For the lysis procedure to obtain nucleic acids, or concentrating nucleic acid from samples, reference may be made to Sambrook, J., et al., Molecular cloning: A Laboratory Manual, (2001) 3rd edition, Cold Spring Harbor Laboratory Press, Cold Spring Harbor, N.Y. Ausubel, F. M., et al., Current Protocols in Molecular Biology (1987), J. Wiley and Sons, New York.

The test sample is generally obtained from a (human) subject suspected of being tumorigenic. Alternatively the test sample is obtained from a subject undergoing routine examination and not necessarily being suspected of having a disease. Thus patients at risk can be identified before the disease has a chance to manifest itself in terms of symptoms identifiable in the patient.

Alternatively the sample is obtained from a subject undergoing treatment, or from patients being checked for recurrence of disease.

Cancers characterised by hypermethylation of tumour suppressor genes may be treated by reducing methylation within the tumour cells. Various agents may be employed for this purpose, including DNA demethylating agents, DNA methyltransferase inhibitors and HDAC inhibitors. Accordingly, the invention also provides a method for predicting the likelihood of successful treatment of colorectal cancer with a DNA demethylating agent and/or a DNA methyltransferase inhibitor and/or HDAC inhibitor comprising detecting an epigenetic modification in: (a) a panel of at least two genes selected from PHACTR3, NDRG4 and FOXE1, (b) at least one gene selected from LAMA1 and CDO1; or (c) at least one gene selected from GPNMB and MMP2 (in a faecal sample) wherein detection of the epigenetic modification in at least one of the genes in the panel or in the at least one gene is indicative that the likelihood of successful treatment is higher than if the epigenetic modification is not detected.

Similarly, the invention provides a method for predicting the likelihood of resistance to treatment of colorectal cancer with a DNA demethylating agent and/or DNA methyltransferase inhibitor and/or HDAC inhibitor comprising detecting an epigenetic modification in (a) a panel of at least two genes selected from PHACTR3, NDRG4 and FOXE1, (b) at least one gene selected from LAMA1 and CDO1; or (c) at least one gene selected from GPNMB and MMP2 (in a faecal sample) wherein detection of the epigenetic modification in at least one of the genes in the panel or in the at least one gene is indicative that the likelihood of resistance to treatment is lower than if the epigenetic modification is not detected.

Furthermore, there is provided a method of selecting a suitable treatment regimen for colorectal cancer comprising detecting an epigenetic modification in (a) a panel of at least two genes selected from PHACTR3, NDRG4 and FOXE1, (b) at least one gene selected from LAMA1 and CDO1; or (c) at least one gene selected from GPNMB and MMP2 (in a faecal sample) wherein detection of the epigenetic modification in at least one of the genes in the panel or in the at least one gene results in selection of a DNA demethylating agent and/or a DNA methyltransferase inhibitor and/or a HDAC inhibitor for treatment and wherein if the epigenetic modification is not detected, a DNA demethylating agent and/or a DNA methyltransferase inhibitor and/or a HDAC inhibitor is not selected for treatment.

In a related aspect, the invention provides a method for monitoring treatment of colorectal cancer with a DNA demethylating agent and/or a DNA methyltransferase inhibitor and/or HDAC inhibitor comprising detecting an epigenetic modification in (a) a panel of at least two genes selected from PHACTR3, NDRG4 and FOXE1, (b) at least one gene selected from LAMA1 and CDO1; or (c) at least one gene selected from GPNMB and MMP2 (in a faecal sample) wherein detection of a reduction in the (levels of the) epigenetic modification in at least one of the genes in the panel or in the at least one gene as treatment progresses is indicative of successful treatment. Thus, the epigenetic modification may be measured at the start of the treatment and then once or more following treatment, or as treatment progresses, in order to determine if the treatment is achieving the desired effect. A return to lower levels of methylation of the genes is considered indicative of effective treatment. Thus, the method may involve testing samples taken at various time points in order to determine the effect of the treatment. A threshold may be set (i.e. a level of reduction in the epigenetic modification) at which treatment is considered successful and may, therefore, be reduced or terminated.

For all of the relevant methods (pharmacogenetic methods, treatment regimen methods, monitoring methods and methods of treatment) of the invention, the DNA demethylating agent may be any agent capable of alleviating hypermethylation of the relevant genes (and thus up regulating transcription of the genes). The DNA methyltransferase inhibitor may be any suitable inhibitor of DNA methyltransferase activity or expression which is suitable for treating cancer in the presence of methylation of the at least one gene. The DNA methyltransferase inhibitor may, be one which reduces expression of DNMT genes, such as suitable antisense molecules, or double stranded RNA molecules, such as siRNA and miRNA molecules which mediate RNAi for example. The design of a suitable siRNA molecule is within the capability of the skilled person and suitable molecules can be made to order by commercial entities (see for example, www.ambion.com). In embodiments, the DNA methyltransferase gene is (human) DNMT1.

Alternatively, the agent may be a direct inhibitor of DNMTs. Examples include modified nucleotides such as phosphorothioate modified oligonucleotides (fig 6 of Villar-Garea, A. And Esteller, M. DNA demethylating agents and chromatin-remodelling drugs: which, how and why? Current Drug Metabolism, 2003, 4, 11-31) and nucleosides and nucleotides such as cytidine analogues. Suitable examples of cytidine analogues include 5-azacytidine, 5-aza-2'-deoxycytidine, 5-fluouro-2'-deoxycytidine, pseudoisocytidine, 5,6-dihydro-5-azacytidine, arabinofuranosyl-5-azacytosine (known as fazabarine) (see figure 4 of Villar-Garea, A. And Esteller, M. DNA demethylating agents and chromatin-remodelling drugs: which, how and why? Current Drug Metabolism, 2003, 4, 11-31). The DNA methyltransferase inhibitor may comprise Decitabine.

Additional DNMT inhibitors include S-Adenosyl-Methionine (SAM) related compounds like ethyl group donors such as L-ethionine and non-alkylating agents such as S-adenosyl-homocysteine (SAH), sinefungin, (S)-6-methyl-6-deaminosine fungin, 6-deaminosinefungin, N4-adenosyl-N4-methyl-2,4-diaminobutanoic acid, 5'-methylthio-5'-deoxyadenosine (MTA) and 5'-amino-5'-deoxyadenosine (Villar-Garea, A. And Esteller, M. DNA demethylating agents and chromatin-remodelling drugs: which, how and why? Current Drug Metabolism, 2003, 4, 11-31). Useful DNMT inhibitors in the present invention comprise, consists essentially of or consists of 5-azacytidine and/or zebulaine.

Further agents which may alter DNA methylation and which may, therefore, be useful in the present invention as DNA demethylating agents include organohalogenated compounds such as chloroform etc, procianamide, intercalating agents such as mitomycin C, 4-aminobiphenyl etc, inorganic salts of arsenic and selenium and antibiotics such as kanamycin, hygromycin and cefotaxim (Villar-Garea, A. And Esteller, M. DNA demethylating agents and chromatin-remodelling drugs: which, how and why? Current Drug Metabolism, 2003, 4, 11-31).

Many HDAC inhibitors are similarly known in the art. Examples include carboxylic acid based HDAC inhibitors such as valproate and/or butyrate and hydroxamic acid based HDAC inhibitors such as trichostatin A, suberoyl hydroxamic acid (SBHA), 6-(3-chlorophenylureido)caproic hydroxamic acid (3-CI-UCHA), m-carboxycinnamic acid bishydroxylamide (CBHA), suberoylanilide hydroxamic acid (SAHA), azelaic bishydroxamic acid (ABHA), pyroxamide, aromatic sulfonamides bearing a hydroxamic acid group and cyclic-hydroxamic-acid containing peptides.

For each of these additional aspects, the embodiments and optional features of the methods of the invention apply mutatis mutandis and are not repeated for reasons of conciseness. Thus, all methods of detecting an epigenetic modification in the DNA, in particular in the specified genes, including expression and re-expression based assays, may be employed appropriately.

In a further related aspect, the invention provides a method of treating colorectal cancer in a subject comprising administration of a DNA demethylating agent and/or a DNA methyltransferase inhibitor and/or a HDAC inhibitor wherein the subject has been selected for treatment on the basis of a method of the invention. Thus, detecting an epigenetic modification in (a) a panel of at least two genes selected from PHACTR3, NDRG4 and FOXE1, (b) at least one gene selected from LAMA1 and CDO1; or (c) at least one gene selected from GPNMB and MMP2 (in a faecal sample) may be used in order to direct treatment of the subject (from which the sample was taken).

The invention also relates to corresponding kits for carrying out the methods of the invention. Thus, the invention provides a kit for detecting a predisposition to, or the incidence of, colorectal cancer in a faecal sample comprising:

(a) means for detecting the presence of blood in the faecal sample, wherein detection of the presence of blood is indicative of a predisposition to, or the incidence of, colorectal cancer, and (b) means for detecting an epigenetic modification in the DNA contained within the faecal sample, wherein detection of the epigenetic modification is indicative of a predisposition to, or the incidence of, colorectal cancer.

As for the corresponding methods, in certain embodiments, the epigenetic modification is detected in at least one gene selected from PHACTR3, NDRG4, FOXE1, GATA4, GPNMB, TFPI2, SOX17, SYNE1, LAMA, MMP2, OSMR, SFRP2 and CDO1 and thus the means for detecting an epigenetic modification in the DNA are means for detecting an epigenetic modification in at least one gene selected from PHACTR3, NDRG4, FOXE1, GATA4, GPNMB, TFPI2, SOX17, SYNE1, LAMA, MMP2, OSMR, SFRP2 and CDO1 In further embodiments, the epigenetic modification is detected in at least one gene selected from PHACTR3, NDRG4 and FOXE1 and thus the means for detecting an epigenetic modification in the DNA are means for detecting an epigenetic modification in at least one gene selected from PHACTR3, NDRG4 and FOXE1. The epigenetic modification may be detected in a panel of at least two genes selected from PHACTR3, NDRG4 and FOXE1, with detection of the epigenetic modification in at least one of the genes providing an indication of a predisposition to, or incidence of, colorectal cancer. Means may be provided for detecting an epigenetic modification in a panel of genes comprising, consisting essentially of or consisting of PHACTR3, NDRG4 and FOXE1, NDRG4 and FOXE1, PHACTR3 and NDRG4, or PHACTR3 and FOXE1. In some embodiments, the means for detecting an epigenetic change in the panel of genes enable the detection to be carried out in a single reaction. Thus the means may permit multiplexing.

In further embodiments, the epigenetic modification is detected in at least one gene from LAMA1 and CDO1 and thus the means for detecting an epigenetic modification in the DNA are means for detecting an epigenetic modification in at least one gene selected from LAMA1 and CD01. Suitable primers and probes are set forth in table 1.

In further embodiments, the epigenetic modification is detected in at least one gene selected from GPNMB and MMP2 and thus the means for detecting an epigenetic modification in the DNA are means for detecting an epigenetic modification in at least one gene selected from GPNMB and MMP2. Suitable primers and probes are set forth in table 1.

As for the methods, the epigenetic modification is often methylation. Thus, the means for detecting an epigenetic modification in the DNA contained within the faecal sample may comprise, consist essentially of or consist of primers and/or probes which permit the methylation status of the DNA to be determined directly. In specific embodiments, the primers are selected from primers comprising, consisting essentially of or consisting of the nucleotide sequences set forth in table 1. Suitable primer pairs can be selected from the primers listed in the table based upon the gene or genes of interest. In specific embodiments, the kits incorporate primers selected from primers comprising, consisting essentially of or consisting of the nucleotide sequences set forth as as SEQ ID Nos: 1 and 2 (PHACTR3), 4 and 5 (FOXE1), and 7 and 8 (NDRG4). In further specific embodiments, the probes are selected from probes comprising, consisting essentially of or consisting of the nucleotide sequences set forth in table 1. Suitable probes can be selected from the probes listed in the table based upon the gene or genes of interest. In specific embodiments, the kits incorporate probes selected from probes comprising, consisting essentially of or consisting of the nucleotide sequences set forth as SEQ ID Nos: 3 (PHACTR3), 6 (FOXE1), and 9 (NDRG4).

The kit may contain any suitable means for allowing detection of blood in a faecal sample. In particular embodiments, the means for detecting the presence of blood in the faecal sample comprise means for detection of haemoglobin in the faecal sample. These may be chromogenic or immunochemical means. Thus, gum guaiac may be incorporated in the kits for chromogenic detection. Alternatively suitable anti-haemoglobin antibodies, as discussed herein, may be incorporated in the kits of the invention. These components may be provided together with suitable buffers etc. as would be readily appreciated by one skilled in the art.

The kits of the invention may also contain further elements to facilitate sample collection and processing. Thus in certain embodiments, the kit further comprises a sealable vessel for collection of a faecal sample. This vessel may be of a size and construction to permit a subject to directly defecate into the vessel. There may also be provided an additional container to which a removed portion of the sample may be added to allow step (a) to be performed on this separated sample. As mentioned in the methods section, this container may contain or be supplied with an appropriate buffer for protein preservation (to prevent denaturation or degradation of proteins). The kit may also contain suitable means for transfer of the removed portion of the sample to the second container. In view of the fact that the invention may be performed using only a small portion of the (total collected) faecal sample, as discussed herein (for example using as little as approximately 1 g of stool to perform DNA extraction), the second container may be suitably dimensioned to contain such a minimal/portioned sample. The second container may be provided with a suitable collection device, adapted to retrieve and/or deposit an appropriate minimal/portioned sample (as described herein, of approximately 5, 4, 3, 2 or 1 g or less). Suitable tubes and spoons for inclusion in such a kit are known in the art and commercially available. The spoons may be measuring spoons and may be integrated into the tubes in certain embodiments. The container may be dimensioned such that a suitable volume of homogenization buffer (as discussed herein, which discussion applies mutatis mutandis) may be added to the minimal/portioned sample added to the container.

In further embodiments, the kit, or more specifically the means for detecting an epigenetic modification in the DNA, further comprises means for processing a faecal sample. The means for processing a faecal sample comprises a homogenization buffer in certain embodiments. Suitable homogenization buffers are known in the art and commercially available. In related embodiments, the means for processing a faecal sample comprises reagents for extraction/isolation/concentration/purification of DNA. As an example, the QIAamp DNA stool kit available from Qiagen includes suitable components for purification of total DNA from fresh or frozen faecal samples.

In order to permit determination of the methylation status of the DNA, the kits may further comprise a reagent which selectively modifies unmethylated cytosine residues in the DNA contained in the sample to produce detectable modified residues but which does not modify methylated cytosine residues. As discussed above, this permits sequence differences to be detected as an indication of the methylation status of the DNA. Any suitable reagent may be employed. Many examples are known in the art and commercially available. In certain embodiments, the reagent comprises a bisulphite reagent. More specifically, the bisulphite reagent may comprise, consist essentially of or consist of sodium bisulphite.

In a related aspect, the invention also provides a kit for any of:
  (a) detecting a predisposition to, or the incidence of, colorectal cancer in a sample
  (b) monitoring treatment of colorectal cancer with a DNA demethylating agent and/or a DNA methyltransferase inhibitor and/or HDAC inhibitor
  (c) predicting the likelihood of successful treatment of colorectal cancer with a DNA demethylating agent and/or a DNA methyltransferase inhibitor and/or HDAC inhibitor
  (d) predicting the likelihood of resistance to treatment of colorectal cancer with a DNA demethylating agent and/or DNA methyltransferase inhibitor and/or HDAC inhibitor; or
  (e) selecting a suitable treatment regimen for colorectal cancer comprising means for detecting an epigenetic modification in a panel of at least two genes selected from PHACTR3, NDRG4 and FOXE1.

As discussed herein, detection of the methylation status of this panel of genes provides a sensitive and specific means for detecting colorectal cancer. In certain embodiments, the means for detecting an epigenetic modification in a panel of at least two genes selected from PHACTR3, NDRG4 and FOXE1 comprise primers and/or probes which permit the methylation status of the genes to be determined directly. In specific embodiments, the primers are selected from primers comprising, consisting essentially of or consisting of the nucleotide sequences set forth as SEQ ID Nos: 1 and 2 (PHACTR3), 4 and 5 (FOXE1), and 7 and 8 (NDRG4). In further embodiments, the probes are selected from probes comprising, consisting essentially of or consisting of the nucleotide sequences set forth as SEQ ID Nos: 3 (PHACTR3), 6 (FOXE1), and 9 (NDRG4).

Similarly, the invention also provides a kit for any of:
  (a) detecting a predisposition to, or the incidence of, colorectal cancer in a sample
  (b) predicting the likelihood of successful treatment of colorectal cancer with a DNA demethylating agent and/or a DNA methyltransferase inhibitor and/or HDAC inhibitor
  (c) predicting the likelihood of resistance to treatment of colorectal cancer with a DNA demethylating agent and/or DNA methyltransferase inhibitor and/or HDAC inhibitor; or
  (d) selecting a suitable treatment regimen for colorectal cancer comprising means for detecting an epigenetic modification in at least one gene selected from LAMA1 and CDO1

As discussed herein, detection of the methylation status of these genes has been shown herein to provide a sensitive and specific means for detecting colorectal cancer. In certain embodiments, the means for detecting an epigenetic modification in at least one gene selected from LAMA1 and CDO1 comprise primers and/or probes which permit the methylation status of the at least one gene to be determined directly. In specific embodiments, the primers are selected from primers selected from primers comprising, consisting essentially of or consisting of the nucleotide sequences set forth as SEQ ID Nos: 28 and 29 (LAMA1) and 34 and 35 (CDO1). In further embodiments, the probes are selected from probes comprising, consisting essentially of or consisting of the nucleotide sequences set forth as SEQ ID Nos: 30 (LAMA1) and 36 (CD01).

As for the methods, the kits are preferably employed in the context of faecal samples. Thus, the kit further comprises means for processing a faecal sample in certain embodiments. In view of the fact that the invention may be performed using only a small portion of the (total collected) faecal sample, as discussed herein (for example using as little as approximately 1 g of stool to perform DNA extraction), the kits may incorporate a container suitably dimensioned to contain such a minimal/portioned sample. The container may be provided with a suitable collection device, adapted to retrieve and/or deposit an appropriate minimal/portioned sample (as described herein, of approximately 5, 4, 3, 2 or 1 g or less). Suitable tubes and spoons for inclusion in such a kit are known in the art and commercially available. The spoons may be measuring spoons and may be integrated into the tubes in certain embodiments. The container may be dimensioned such that a suitable volume of homogenization buffer (as discussed herein, which discussion applies mutatis mutandis) may be added to the minimal/portioned sample added to the container.

The invention also provides a kit for any of:
  (a) detecting a predisposition to, or the incidence of, colorectal cancer in a sample
  (b) predicting the likelihood of successful treatment of colorectal cancer with a DNA demethylating agent and/or a DNA methyltransferase inhibitor and/or HDAC inhibitor
  (c) predicting the likelihood of resistance to treatment of colorectal cancer with a DNA demethylating agent and/or DNA methyltransferase inhibitor and/or HDAC inhibitor; or
  (d) selecting a suitable treatment regimen for colorectal cancer comprising means for detecting an epigenetic modification in at least one gene selected from GPNMB and MMP2 and means for processing a faecal sample.

As discussed herein, detection of the methylation status of these genes has been shown herein to provide a sensitive and specific means for detecting colorectal cancer in the context of faecal samples. In certain embodiments, the means for detecting an epigenetic modification in at least one gene selected from GPNMB and NMP1 comprise primers and/or probes which permit the methylation status of the at least one gene to be determined directly. In specific embodiments, the primers are selected from primers selected from primers comprising, consisting essentially of or consisting of the nucleotide sequences set forth as SEQ ID Nos: 22 and 23 (GPNMB) and 31 and 32 (MMP2). In further embodiments, the probes are selected from probes comprising, consisting essentially of or consisting of the nucleotide sequences set forth as SEQ ID Nos: 24 (GPNMB) and 33 (MMP2).

In specific embodiments of these kits of the invention which involve means for processing a faecal sample, the means for processing a faecal sample comprises a sealable vessel for collection of a faecal sample. This vessel may be of a size and construction to permit a subject to directly defecate into the vessel. In view of the fact that the invention may be performed using only a small portion of the (total collected) faecal sample, as discussed herein (for example using as little as approximately 1 g of stool to perform DNA extraction), the kits may incorporate a container suitably dimensioned to contain such a minimal/portioned sample. The container may be provided with a suitable collection device, adapted to retrieve and/or deposit an appropriate minimal/portioned sample (as described herein, of approximately 5, 4, 3, 2 or 1 g or less).

Suitable tubes and spoons for inclusion in such a kit are known in the art and commercially available. The spoons may be measuring spoons and may be integrated into the tubes in certain embodiments. The container may be dimensioned such that a suitable volume of homogenization buffer (as discussed herein, which discussion applies mutatis mutandis) may be added to the minimal/portioned sample added to the container.

In further embodiments, the means for processing a faecal sample comprises a homogenization buffer in certain embodiments. Suitable homogenization buffers are known in the art and commercially available. In related embodiments, the means for processing a faecal sample may (further) comprise reagents for extraction/isolation/concentration/purification of DNA from the faecal sample. As an example, the QIAamp DNA stool kit available from Qiagen includes suitable components for purification of total DNA from fresh or frozen faecal samples.

In order to permit determination of the methylation status of the panel of genes, the kits may further comprise a reagent which selectively modifies unmethylated cytosine residues in the DNA contained in the sample to produce detectable modified residues but which does not modify methylated cytosine residues. As discussed above, this permits sequence differences to be detected as an indication of the methylation status of the DNA. Any suitable reagent may be employed. Many examples are known in the art and commercially available. In certain embodiments, the reagent comprises a bisulphite reagent. More specifically, the bisulphite reagent may comprise, consist essentially of or consist of sodium bisulphite.

EXPERIMENTAL SECTION

Example 1

Sample Collection and Processing

A standardized multicenter screening trial (The Netherlands) was initiated in 2006. In this trial, non symptomatic subjects aged 50 or above are screened with colonoscopy, FOBT and real-time MSP using DNA from stool and blood. In addition, prospectively collected stool samples from multiple centers (Germany and The Netherlands) were used. In these trials, symptomatic patients, attending a Gastroenterology clinic and ultimately diagnosed with CRC, provided a stool sample for use in real-time MSP. From the ongoing trials 111 stool samples were available for the present study. 3 main categories of stool samples were used: 38 samples with no suspicious findings, 10 adenomas and 63 samples from patients covering all stages of CRC. After defecation in a special bucket, an iFOBT samples was taken (Eiken device) and the patients subsequently added 250 ml of stool homogenization buffer (Amresco, Solon, Ohio, USA) to the sample. Samples were shipped to the laboratory and further processed within 72 hours after defecation. Stool homogenization buffer was added to a ratio 1:7, and the samples were homogenized and aliquoted in portions of 32 ml.

iFOBT

The OC-Hemodia 'Eiken' was used to detect faecal occult blood when screening for early identification of colon cancer DNA Extraction from Stool Single aliquots (32 ml containing the equivalent of 4 g of stool) were centrifuged for 5 minutes at 2540 rcf at 20° C. The supernatant was retained and centrifuged a second time (10 minutes at 16500 rcf at 4° C.). 22 ml of the supernatant obtained following the second centrifugation step was incubated with 5 µl Rnase A for 60 minutes at 37° C. Total DNA was then SodiumAcetate (pH 5.2)—isopropanol precipitated and washed with 70% ethanol. This "crude DNA" was resuspended in 4 ml 1×TE (pH 7.4). For set A (QIAamp DNA Stool Mini Kit): Add 1.6 ml ASL Buffer to 300 µl "crude DNA" and vortex. The samples were centrifuged to pellet remaining stool particles. 1.4 ml of this supernatant was transferred into a new microcentrifuge tube. One InhibitEX Tablet was dissolved in each sample before a 1 min incubation step to allow inhibitors to adsorb to the InhibitEX matrix. The samples were then centrifuged to pellet all remaining stool particles and inhibitors bound to InhibitEX matrix. The supernatant was transferred into a new microcentrifuge tube. 25 µl of proteinase K was added to 600 ul of sample supernatant before adding 600 µl of AL Buffer. The tubes are incubated at 70° C. for 10 min. 600 µl of ethanol (96-100%) were added to the lysate, and mix by vortexing. Carefully apply 3×600 µl of lysate to QIAamp spin columns, centrifuge and discard the tube containing the filtrate. Carefully open the QIAamp spin column and add 500 µl of AW1 Buffer, centrifuge and discard the collection tube containing the filtrate. Carefully open the QIAamp spin column and add 500 µl of AW2 Buffer, centrifuge discard the collection tube containing the filtrate. Transfer the QIAamp spin column into a new microcentrifuge tube, open the QIAamp spin column, add 50 µl of AE Buffer onto the membrane, incubate for 1 min at room temperature, and then centrifuge to elute DNA. For set B (QIAamp DNA Stool Midi Kit): Add 1.5 ml ASL buffer to 2 ml of "Crude DNA". Add 1 inhibitEX Tablet to each sample and vortex IMMEDIATELY and continuously for 1 min or until the tablet is completely suspended. Incubate suspension for 1 min at room temperature to allow inhibitors to adsorb to the InhibitEX matrix. Centrifuge sample to pellet stool particles and inhibitors bound to InhibitEX matrix. Collect the supernatant and transfer it into a new 15 ml centrifuge tube, discard the pellet.

Add 150 µl proteinase K to 2 ml of the supernatant, mix well, add 2.4 ml of AL Buffer and vortex for 15 s. Incubate at 70° C. for 10 min. Add 2 ml ethanol (96-100%) to the sample, and mix by inverting the tube 10 times, followed by additional vigorous shaking. In order to ensure efficient binding, it is essential that the sample is mixed thoroughly after addition of ethanol to yield a homogeneous solution.

Carefully transfer 3.3 ml of the sample onto the QIAamp Midi column placed in a 15 ml centrifuge tube and centrifuge at 1850×g (3000 rpm) for 3 min, and discard the filtrate. Place the QIAamp midi column back into the 15 ml centrifuge tube. Load the remainder of the sample onto the QIAamp Midi column, centrifuge again at 1850×g (3000 rpm) for 3 minutes, and discard the filtrate. Place the QIAamp Midi column back into the 15 ml centrifuge tube, add 2 ml of AW1 Buffer, centrifuge at 4500×g (5000 rpm) for 1 min, add 2 ml of AW2 Buffer to the QIAamp Midi column, centrifuge at 4500×g (5000 rpm) for 15 min, and discard the filtrate. Place the QIAamp Midi column in a clean 15 ml centrifuge tube, centrifuge for 1 min to dry the column, place the QIAamp Midi column in a clean 15 ml centrifuge tube, and discard the collection tube containing the filtrate.

Add 200 µl of AE Buffer directly onto the membrane of the QIAamp Midi column, incubate at room temperature for 5 min, and centrifuge at 4500×g (5000 rpm) for 2 min. Reload the same 200 µl onto the membrane, incubate at room temperature for 5 min, and centrifuge at 4500×g (5000 rpm) for 2 min to elute the DNA.

DNA Modification 1.5 µg of DNA were subjected to bisulfite modification in 96-wells format on a pipetting robot (Tecan), using the EZ-96DNA Methylation kit (Zymo Research), according to the manufacturer's protocol. Basically, aliquots of 45 µl were mixed with 5 µl of M-Dilution Buffer and incubated at 37° C. for 15 minutes shaking at 1100 rpm. Then 100 µl of the diluted CT Conversion Reagent was added and samples were incubated at 70° C. for 3 hours, shaking at 1100 rpm in the dark. After conversion, the samples were desalted by incubation on ice for 10 minutes and addition of 400 µl of M-Binding buffer. The samples were loaded on a Zymo-Spin I Column in a collection tube and after centrifugation washed with 200 µl of M-Wash Buffer. 200 µl of M-Desulphonation Buffer was put onto the column and incubated at room temperature for 15 minutes. After centrifugation of the columns, they were washed twice with 200 µl of M-Wash Buffer. Finally, the DNA was washed from the column in 50 µl Tris-HCl 1 mM pH8.0 and stored at −80° C., until further processing.

DNA Amplification

Real-time MSP was applied on a 7900HT fast real-time PCR system (Applied Biosystems). 5 ul or 10 ul of the modified DNA was added to a PCR mix (total volume 25 or 50 uI) containing buffer (16.6 mM (NH4)2SO4, 67 mM Tris (pH 8.8), 6.7 mM MgCl2, 10 mM (3-mercaptoethanol), dNTPs (5 mM), forward primer (6 ng), reverse primer (18 ng), molecular beacon (0.16 µM), BSA (0.1 µg), and Jumpstart DNA Taq polymerase (0.4 units; Sigma Aldrich). The primer sequences and molecular beacon sequences used for each of the genes are summarized in table 1. Cycle program used was as follows: 5 minutes 95° C., followed by 45 cycles of 30 seconds 95° C., 30 seconds 57° C. (51° C. for APC), and 30 seconds 72° C., followed by 5 minutes 72° C. A standard curve (2×106—20 copies) was included to determine copy numbers of unknown samples by interpolation of their Ct values to the standard curve.

Results

TABLE 1

Primers sequences and beacon sequences (for sample sets A and B)

| Gene | Primer or probe | Nucleotide sequence (including labels on probe) | SEQ ID NO: |
|---|---|---|---|
| PHACTR | forward primer | 5'-TTATTTTGCGAGCGGTTTC-3' | 1 |
|  | reverse primer | 5'-GAATACTCTAATTCCACGCGACT-3' | 2 |
|  | beacon | 5'-FAM-CGACATGCGGGTTCGGTCGGCGCGGGGCATGTCG-3'-DABCYL | 3 |
| FOXE1 | forward primer | 5'-TTTGTTCGTTTTTCGATTGTTC-3' | 4 |
|  | reverse primer | 5'-TAACGCTATAAAACTCCTACCGC-3' | 5 |
|  | beacon | 5'-FAM-CGTCTCGTCGGGGTTCGGGCGTATTTTTTAGGTAGGCGAGACG-3'-DABCYL | 6 |
| NDRG4 | forward primer | 5'-GTATTTTAGTCGCGTAGAAGGC-3' | 7 |
|  | reverse primer | 5'-AATTTAACGAATATAAACGCTCGAC-3' | 8 |
|  | beacon | 5'-FAM-CGACATGCCCGAACGAACCGCGATCCCTGCATGTCG-3'-DABCYL | 9 |
| GATA4 | Forward primer | 5'-AGGTTAGTTAGCGTTTTAGGGTC-3' | 10 |
|  | Reverse primer | 5'-ACGACGACGAAACCTCTCG-3' | 11 |
|  | beacon | 5'-FAM-CGACATGCCTCGCGACTCGAATCCCCGACCCAGCATGTCG-DABCYL-3' | 12 |

TABLE 1-continued

Primers sequences and beacon sequences (for sample sets A and B)

| Gene | Primer or probe | Nucleotide sequence (including labels on probe) | SEQ ID NO: |
|---|---|---|---|
| OSMR | Forward primer | 5'-TTTGGTCGGGGTAGGAGTAGC-3' | 13 |
| | Reverse primer | 5'-CGAACTTTACGAACGAACGAAC-3' | 14 |
| | beacon | 5'-FAM-CGACATGCCCGTACCCCGCGCAGCATGTCG-3'-DABCYL | 15 |
| SYNE1 | Forward primer | 5'-GTTGGGTTTTCGTAGTTTTGTAGATCGC-3' | 16 |
| | Reverse primer | 5'-CTACGCCCAAACTCGACG-3' | 17 |
| | beacon | 5'-FAM-CGACATGCCCCGCCCTATCGCCGAAATCGCATGTCG-DABCYL-3' | 18 |
| SFRP2 | Forward primer | 5'-GGGTCGGAGTTTTTCGGAGTTGCGC-3' | 19 |
| | Reverse primer | 5'-CCGCTCTCTTCGCTAAATACGACTCG-3' | 20 |
| | beacon | 5'-FAM-CGACATGCGGTGTTTCGTTTTTTCGCGTTTTAGTCGTCGGGCATGTCG-DABCYL-3' | 21 |
| GPNMB | Forward primer | 5'-GGTCGTAGTCGTAGTCGGG-3' | 22 |
| | Reverse primer | 5'-CCGCAAAAACCTAAAACGTAA-3' | 23 |
| | beacon | 5'-FAM-CGACATGCGGTTTTTTGGGTCGGGGCGCGGCATGTCG-DABCYL-3' | 24 |
| SOX17 | Forward primer | 5'-GAGATGTTTCGAGGGTTGC-3' | 25 |
| | Reverse primer | 5'-CCGCAATATCACTAAACCGA-3' | 26 |
| | beacon | 5'-FAM-CGACATGCGTTCGTGTTTTGGTTTGTCGCGGTTTGGCATGTCG DABCYL-3' | 27 |
| LAMA1 | Forward primer | 5'-TTTTTAGATTTATCGAGTGGCG-3' | 28 |
| | Reverse primer | 5'-CGAACTCACCTCTCTACCGAC-3' | 29 |
| | beacon | 5'-CGACATGCCAAAAACACGCCCCCGCGCATGTCG-3' | 30 |
| MMP2 | Forward primer | 5'-TTCGGGTTATTAGCGTTTTTATC-3' | 31 |
| | Reverse primer | 5'-ACTCCAACCAAACGACGAA-3' | 32 |
| | beacon | 5'-FAM-CGACATCGTTGGTTCGGTGCGTGTGGTCGATGTCG-DABCYL-3' | 33 |
| CDO1 | Forward primer | 5'-AATTTGATTTGTGTGTATCGC-3' | 34 |
| | Reverse primer | 5'-GAAACGTAAAAATATCGTCGCA-3' | 35 |
| | beacon | 5'-FAM-CGACATGCGCGATTTCGGATTTATTGCGTTGTTAGGGCATGTCG-DABCYL-3' | 36 |

TABLE 1-continued

Primers sequences and beacon sequences (for sample sets A and B)

| Gene | Primer or probe | Nucleotide sequence (including labels on probe) | SEQ ID NO: |
|---|---|---|---|
| TFPI2 | Forward primer | 5'-GTTCGTTGGGTAAGGCGTTC-3' | 37 |
|  | Reverse primer | 5'-CATAAAACGAACACCCGAACCG-3' | 38 |
|  | Beacon | 5'-FAM-CGACATGCACCGCGCACCTCCTCCCGCCAAGCATGTCG-DABCYL-3' | 39 |

Performance of the Individual Methylation Markers in Fecal Samples (Set A)

Twelve methylation markers (GATA4, GPNMB, TFPI2, FoxE1, SOX17, SYNE1, NDRG4, LAMA, MMP2, PHACTR, OSMR and CDO1) were evaluated in fecal samples. Methylated copies of these genes were quantified in the available stool samples by real-time MSP on a 7900HT fast real-time PCR system (Applied Biosystems).

The individual performances of the twelve genes in fecal samples are shown in Table 2. The best performing gene in faecal samples from patients with CRC corresponded to NDRG4 with 61% sensitivity with a corresponding specificity of 100%.

TABLE 2

Performance of the individual methylation markers in faecal samples set A using a certain cutoff (gene copies).

| Gene | cutoff | Spec (n = 21) | Sens (n = 23) |
|---|---|---|---|
| GATA4 | 10 | 90% | 52% |
| GPNMB | 100 | 100% | 39% |
| TFPI2 | 100 | 100% | 48% |
| FoxE1 | 5 | 100% | 39% |
| SOX17 | 10 | 90% | 35% |
| SYNE1 | 3 | 90% | 43% |
| NDRG4 | 2 | 100% | 61% |
| LAMA | 40 | 100% | 30% |
| MMP2 | 10 | 95% | 39% |
| PHACTR | 100 | 100% | 43% |
| OSMR | 1 | 95% | 22% |
| CDO1 | 10 | 95% | 13% |

Performance of the 3 Methylation Marker Combination in Fecal Samples Set A

The performance of combinations of three methylation markers was also investigated. Methylated copies of the genes were quantified in the available stool samples by real-time MSP on a 7900HT fast real-time PCR system (Applied Biosystems). Table 3 shows the results and lists the cut-off (copies) applied. The best combinations had 100% specificity, 70% sensitivity for CRC.

TABLE 3

Performance of 3 methylation marker combinations in set A (top 3 rows give the cutoffs, empty cells denote that the gene was not used). A sample is scored as positive if any one marker is positive.

| NDRG4 (copies) | 2 | 2 |  | 2 |
|---|---|---|---|---|
| FOXE1 (copies) | 0 | 0 | 0 |  |
| PHACTR (copies) |  | 100 | 100 | 100 |
| Spec (n = 21) | 100% | 100% | 100% | 100% |
| Sens (n = 23) | 70% | 70% | 52% | 65% |

Performance of FIT in Fecal Samples (Set A)

FIT was evaluated in the same fecal samples. The performance in fecal samples is shown in Table 4. A specificity of 95% and sensitivity of 78% was obtained.

TABLE 4

Performance of FIT in fecal samples set A

|  | FIT |
|---|---|
| Cutoff (ng/ml) | 100 |
| Spec (n = 21) | 95% |
| Sens (n = 23) | 78% |

Performance of the 3 Methylation Marker Combination AND FIT in Fecal Samples Set A The performance of combination of the methylation markers with FIT was investigated. Methylated copies of the genes were quantified in the available stool samples by real-time MSP on a 7900HT fast real-time PCR system (Applied Biosystems). Table 5 shows the results and lists the cut-off (copies) applied.

TABLE 5

Performance of the methylation marker combinations in set A. A sample is scored as positive if any one marker is positive.

| Gene | cutoffs (copies) | Methylation marker only | | Methylation markers plus FIT (100 ng/ml cutoff) | |
|---|---|---|---|---|---|
|  |  | Spec (n = 21) | Sens (n = 23) | Spec (n = 21) | Sens (n = 23) |
| GATA4 | 10 | 90% | 52% | 86% | 87% |
| GPNMB | 100 | 100% | 39% | 95% | 87% |
| TFPI2 | 100 | 100% | 48% | 95% | 91% |
| FoxE1 | 5 | 100% | 39% | 95% | 87% |
| SOX17 | 10 | 90% | 35% | 86% | 87% |
| SYNE1 | 3 | 90% | 43% | 86% | 91% |
| NDRG4 | 2 | 100% | 61% | 95% | 87% |
| LAMA | 40 | 100% | 30% | 95% | 83% |
| MMP2 | 10 | 95% | 39% | 90% | 87% |
| PHACTR | 100 | 100% | 43% | 95% | 87% |
| OSMR | 1 | 95% | 22% | 90% | 83% |
| CDO1 | 10 | 95% | 13% | 90% | 83% |

Performance of the Methylation Marker Combination AND FIT in Fecal Samples Set A The performance of a combination of the methylation markers with FIT was investigated, the results are shown in table 6.

TABLE 6

Performance of 3 methylation marker combinations in set A (top 4 rows give the cutoffs, empty cells denote that the gene was not used). A sample is scored as positive if any one marker is positive.

| | | | | |
|---|---|---|---|---|
| FIT (ng/ml) | 100 | 100 | 100 | 100 |
| NDRG4 (copies) | 2 | 2 | | 2 |
| FOXE1 (copies) | 0 | 0 | 0 | |
| PHACTR (copies) | 100 | | 100 | 100 |
| Spec (n = 21) | 95% | 95% | 95% | 95% |
| Sens (n = 23) | 96% | 96% | 91% | 91% |

Performance of Methylation Markers in Fecal Samples (Set B)

Seven methylation markers (NDRG4, FoxE1, PHACTR, GATA4, OSMR, SYNE1, SFRP2) were evaluated in fecal samples. Methylated copies of these genes were quantified in the available stool samples by real-time MSP on a 7900HT fast real-time PCR system (Applied Biosystems). The individual performances of the 7 genes are shown in Table 7. The best performing gene in fecal samples from patients with CRC corresponded to PHACTR with 68% sensitivity with a corresponding specificity of 100%.

TABLE 7

Performance of the individual methylation markers in fecal samples set B

| Gene | NDRG4 | FoxE1 | PHACTR | GATA4 | OSMR | SYNE1 | SFRP2 |
|---|---|---|---|---|---|---|---|
| cutoff | 2 | 0 | 100 | 10 | 1 | 3 | 2 |
| Specificity | 100% | 94% | 100% | 100% | 88% | 100% | 100% |
| Sensitivity for advanced adenoma | 0% | 0% | 10% | 10% | 20% | 10% | 10% |
| Sensitivity for CRC | 35% | 55% | 68% | 43% | 45% | 65% | 58% |

Performance of FIT in Fecal Samples (Set B)

FIT was evaluated in the same fecal samples. The performance in fecal samples is shown in Table 8.

TABLE 8

Performance of FIT in fecal samples set B

| | FIT |
|---|---|
| Cutoff (ng/ml) | 100 |
| Specificity | 100% |
| Sensivity for advanced adenoma | 10% |
| Sensivity for CRC | 78% |

The FIT obtained a sensitivity of 78% and a corresponding specificity of 100%

Performance of the Methylation Markers and Combinations Thereof with or without FIT in Fecal Samples Set B The performance of combination of 3 methylation markers was investigated with or without FIT. Methylated copies of the genes were quantified in the available stool samples by real-time MSP on a 7900HT fast real-time PCR system (Applied Biosystems). Table 9 shows the results and lists the cut-off (copies) applied.

TABLE 9

Performance of the 3 methylation marker combinations in set B

| | | | | | | | | |
|---|---|---|---|---|---|---|---|---|
| FIT (ng/ml) | 100 | 100 | 100 | 100 | | | | |
| NDRG4 (copies) | 2 | 2 | | 2 | 2 | 2 | | 2 |
| FOXE1 (copies) | 0 | 0 | 0 | | 0 | 0 | 0 | |
| PHACTR (copies) | 100 | | 100 | 100 | 100 | | 100 | 100 |
| Spec (n = 17) | 94% | 94% | 94% | 100% | 94% | 94% | 94% | 100% |
| Sens adv adenoma (n = 10) | 20% | 20% | 20% | 20% | 10% | 0% | 10% | 10% |
| Sens CRC (n = 40) | 95% | 88% | 95% | 95% | 70% | 58% | 70% | 68% |

Use of FIT as First Line Screening and Methylation as a Second Line Confirmation Assay A simulation was made wherein the FIT test would be used a screening test and whereby a low cutoff of 10 ng/ml would be used to maximize the sensitivity. For samples with more than 10 ng/ml hemoglobin and less than 200 ng/ml the methylation test can be used to increase the specificity for this subgroup. Samples are scored as positive if the FIT value is higher than 200 ng/ml or if one of the methylation markers is positive.

Table 10 shows the sensitivity and specificity of the FIT test as a first line test, as well as the overall sensitivity and specificity of the combination of FIT as first line and confirmation with "FIT>200 OR a positive result on a methylation panel consisting of three genes".

Results for panel A when only applying the combination of FIT and methylation markers to samples having more than >10 and less than 200 ng/ml hemoglobin.

| Total number of tested with FIT = 44 | Number of patients to be tested with the methylation panel = 5 | FOXE1 (copies) | 0 |
|---|---|---|---|
| | | NDRG4 (copies) | 0 |
| | | PHACTR (copies) | 50 |
| | | Spec (n = 21) | 95% |
| | | Sens (n = 23) | 83% |

Results for panel B when only applying the combination of FIT and methylation markers to samples having more than >10 and less than 200 ng/ml hemoglobin.

| Total number of tested with FIT = 67 | Number of patients to be tested with the methylation panel = 12 | FOXE1 (copies) | 0 |
|---|---|---|---|
| | | NDRG4 (copies) | 0 |
| | | PHACTR (copies) | 50 |
| | | Spec (n = 17) | 94% |
| | | Sens adv adenoma (n = 10) | 20% |
| | | Sens CRC (n = 40) | 88% |

Example 2

FIT and Methylation Testing on Partial Stool Samples

In Example 1 homogenates of whole stool sample material were investigated. In this example, the inventor evaluated whether sufficient DNA material could be subtracted from partial stool samples allowing subsequent methylation analysis.

Sample Collection and Nucleic Acid Isolation 82 historical stool samples, collected between 2003 and 2008, were available for the present study. The samples were frozen down at the time of collection without addition of stabilizing buffer and stored at −20° C. until further use.

In this study only a portion of the stool sample (≈1 g) was investigated for further methylation testing. First, historical samples were thawed at the storage site and partial samples were taken 1 g) using special designed stool tubes with integrated measuring spoons (Sarstedt). Each sample was then weighted and 2 volumes of stabilizing buffer (Diagn MoI Pathol; Volume 14, Number 3, September 2005) were added. Samples were stored at −80° C. until the complete sample set was ready for transfer to the processing site.

DNA from these samples was prepared using the QiaAmp DNA stool minikit (Qiagen) following the same procedure as detailed in example 1, sample set A. Adapted volumes were used for starting material and elution: 3 DNA isolations were done per stool sample, processing 250 µl of homogenized stool material each, and elute in 75 µl of buffer AE. At the end, eluates of the same sample were pooled and DNA was quantified using the Picogreen® dsDNA quantitation kit (Molecular Probes, #P7589) following the manufacturer's directions.

DNA Modification and Amplification

Samples were subjected to bisulfite modification using a commercially available kit (i.e. Zymo, #D5002) as discussed in example 1. Again, input material and elution volume were slightly adapted for this study: up to 2 µg of input DNA was used and elution was done in 30 µl Tris-HCl (1 mM, pH 8.0); samples were stored at −80° C., until further processing.

Real-time MSP was performed as set out in example 1. DNA methylation patterns of the PHACTR3 gene were determined by chemical modification of unmethylated but not the methylated cytosines to uracil and subsequent PCR using primers specific for the methylated version, sequence details are provided in Table 1.

Results Methylation status for patients was studied in DNA extracted from partial stool samples derived from historical faecal collections. Average yield of DNA was 7 µg (ranging from 0.3 to 27 µg, SD 5 µg) resulting in sufficient DNA material for subsequent bisulfite modification and real-time MSP procedure. Methylated copies of the PHACTR3 genes were quantified in the available stool portions. Performance of this methylation marker and combination with or without FIT were comparable with the above reported data from the prospectively collected whole stool sample set.

The present invention is not to be limited in scope by the specific embodiments described herein. Indeed, various modifications of the invention in addition to those described herein will become apparent to those skilled in the art from the foregoing description and accompanying figures. Such modifications are intended to fall within the scope of the appended claims. Moreover, all embodiments described herein are considered to be broadly applicable and combinable with any and all other consistent embodiments, as appropriate.

I claim:

1. A method of processing a freshly-collected fecal sample without freezing, the method comprising:
   a) collecting a fecal sample from a human subject, wherein the fecal sample is collected at home by the human subject by defecation directly into a sealable collection vessel;
   b) removing a portion of said fecal sample to a separate container to produce a removed portion and a remaining portion of said fecal sample;
   c) combining the removed portion in the separate container with a buffer that prevents denaturation or degradation of blood proteins found in a fecal sample; and
   d) stabilizing the remaining portion of the fecal sample by adding a buffer that maintains DNA integrity in a fecal sample to the remaining portion in the sealable collection vessel.

2. The method of claim 1, further comprising delivering the container containing the removed portion and buffer and the sealable vessel containing the remaining portion of the fecal sample and buffer to a medical diagnostics laboratory.

3. A method of processing a fecal sample, the method comprising:
- A) obtaining a pair of portions of a fecal sample from a human subject, the pair of portions comprising a container containing a removed portion and a buffer, and a sealable vessel containing a stabilized remaining portion of a fecal sample and a buffer obtained by the method of claim 1;
- B) testing the removed portion of said fecal sample for a concentration of hemoglobin present in said removed portion;
- C) extracting DNA from the remaining portion of said fecal sample; and
- D) analyzing said DNA for the presence of DNA from the human subject having an epigenetic modification.

4. The method of claim 3, wherein testing for the concentration of hemoglobin in said removed portion comprises immunochemical detection of hemoglobin.

5. The method of claim 3, wherein the removed portion of said fecal sample is considered positive for the presence of blood when the concentration of hemoglobin detected in said removed portion is at least 5 ng/ml.

6. The method of claim 3, wherein the removed portion of said fecal sample is considered positive for the presence of blood when the concentration of hemoglobin detected in said removed portion is at least 10 ng/ml.

7. The method of claim 3, wherein the removed portion of said fecal sample is considered positive for the presence of blood when the concentration of hemoglobin detected in said removed portion is at least 20 ng/ml.

8. The method of claim 3, wherein the removed portion of said fecal sample is considered positive for the presence of blood when the concentration of hemoglobin detected in said removed portion is at least 50 ng/ml.

9. The method of claim 3, wherein the removed portion of said fecal sample is considered positive for the presence of blood when the concentration of hemoglobin detected in said removed portion is at least 200 ng/ml.

10. The method of claim 3, wherein said epigenetic modification comprises aberrant methylation.

11. The method of claim 3, wherein said aberrant methylation comprises hypermethylation.

12. The method of claim 3, wherein said DNA from the human subject comprises a gene and/or a promoter region of a gene.

13. The method of claim 12, wherein said gene is selected from the group consisting of PHACTR3, NDRG4, FOXE1, GATA4, GPNMB, TFPI2, SOX17, SYNE1, LAMA, MMP2, OSMR, SFRP2, and CDO1.

14. The method of claim 10, wherein analyzing said DNA comprises modifying said DNA with bisulfite ions under conditions wherein unmethylated cytosine is converted to uracil.

* * * * *

SEQUENCE LISTING

<160> NUMBER OF SEQ ID NOS: 39

<210> SEQ ID NO 1
<211> LENGTH: 19
<212> TYPE: DNA
<213> ORGANISM: Artificial sequence
<220> FEATURE:
<223> OTHER INFORMATION: Primer

<400> SEQUENCE: 1
ttattttgcg agcggtttc

```
<210> SEQ ID NO 2
<211> LENGTH: 23
<212> TYPE: DNA
<213> ORGANISM: Artificial sequence
<220> FEATURE:
<223> OTHER INFORMATION: Primer

<400> SEQUENCE: 2
gaatactcta attccacgcg act                                            23

<210> SEQ ID NO 3
<211> LENGTH: 34
<212> TYPE: DNA
<213> ORGANISM: Artificial sequence
<220> FEATURE:
<223> OTHER INFORMATION: Probe

<400> SEQUENCE: 3
cgacatgcgg gttcggtcgg cgcggggcat gtcg                                34

<210> SEQ ID NO 4
<211> LENGTH: 22
<212> TYPE: DNA
<213> ORGANISM: Artificial sequence
<220> FEATURE:
<223> OTHER INFORMATION: Primer

<400> SEQUENCE: 4
tttgttcgtt tttcgattgt tc                                             22

<210> SEQ ID NO 5
<211> LENGTH: 23
<212> TYPE: DNA
<213> ORGANISM: Artificial sequence
<220> FEATURE:
<223> OTHER INFORMATION: Primer

<400> SEQUENCE: 5
taacgctata aaactcctac cgc                                            23

<210> SEQ ID NO 6
<211> LENGTH: 44
<212> TYPE: DNA
<213> ORGANISM: Artificial sequence
<220> FEATURE:
<223> OTHER INFORMATION: Probe

<400> SEQUENCE: 6
cgtctcgtcg gggttcgggc gtattttttt aggtaggcga gacg                     44

<210> SEQ ID NO 7
<211> LENGTH: 22
<212> TYPE: DNA
<213> ORGANISM: Artificial sequence
<220> FEATURE:
<223> OTHER INFORMATION: Primer

<400> SEQUENCE: 7
gtattttagt cgcgtagaag gc                                             22

<210> SEQ ID NO 8
<211> LENGTH: 25
<212> TYPE: DNA
<213> ORGANISM: Artificial sequence
<220> FEATURE:
<223> OTHER INFORMATION: Primer
```

```
<400> SEQUENCE: 8
aatttaacga atataaacgc tcgac                                          25

<210> SEQ ID NO 9
<211> LENGTH: 36
<212> TYPE: DNA
<213> ORGANISM: Artificial sequence
<220> FEATURE:
<223> OTHER INFORMATION: Probe

<400> SEQUENCE: 9
cgacatgccc gaacgaaccg cgatccctgc atgtcg                              36

<210> SEQ ID NO 10
<211> LENGTH: 23
<212> TYPE: DNA
<213> ORGANISM: Artificial sequence
<220> FEATURE:
<223> OTHER INFORMATION: Primer

<400> SEQUENCE: 10
aggttagtta gcgttttagg gtc                                            23

<210> SEQ ID NO 11
<211> LENGTH: 19
<212> TYPE: DNA
<213> ORGANISM: Artificial sequence
<220> FEATURE:
<223> OTHER INFORMATION: Primer

<400> SEQUENCE: 11
acgacgacga aacctctcg                                                 19

<210> SEQ ID NO 12
<211> LENGTH: 40
<212> TYPE: DNA
<213> ORGANISM: Artificial sequence
<220> FEATURE:
<223> OTHER INFORMATION: Probe

<400> SEQUENCE: 12
cgacatgcct cgcgactcga atccccgacc cagcatgtcg                          40

<210> SEQ ID NO 13
<211> LENGTH: 21
<212> TYPE: DNA
<213> ORGANISM: Artificial sequence
<220> FEATURE:
<223> OTHER INFORMATION: Primer

<400> SEQUENCE: 13
tttggtcggg gtaggagtag c                                              21

<210> SEQ ID NO 14
<211> LENGTH: 22
<212> TYPE: DNA
<213> ORGANISM: Artificial sequence
<220> FEATURE:
<223> OTHER INFORMATION: Primer

<400> SEQUENCE: 14
cgaactttac gaacgaacga ac                                             22
```

```
<210> SEQ ID NO 15
<211> LENGTH: 32
<212> TYPE: DNA
<213> ORGANISM: Artificial sequence
<220> FEATURE:
<223> OTHER INFORMATION: Probe

<400> SEQUENCE: 15
cgacatgccc gtaccccgcg cgcagcatgt cg                                    32

<210> SEQ ID NO 16
<211> LENGTH: 28
<212> TYPE: DNA
<213> ORGANISM: Artificial sequence
<220> FEATURE:
<223> OTHER INFORMATION: Primer

<400> SEQUENCE: 16
gttgggtttt cgtagttttg tagatcgc                                         28

<210> SEQ ID NO 17
<211> LENGTH: 18
<212> TYPE: DNA
<213> ORGANISM: Artificial sequence
<220> FEATURE:
<223> OTHER INFORMATION: Primer

<400> SEQUENCE: 17
ctacgcccaa actcgacg                                                    18

<210> SEQ ID NO 18
<211> LENGTH: 36
<212> TYPE: DNA
<213> ORGANISM: Artificial sequence
<220> FEATURE:
<223> OTHER INFORMATION: Probe

<400> SEQUENCE: 18
cgacatgccc cgccctatcg ccgaaatcgc atgtcg                                36

<210> SEQ ID NO 19
<211> LENGTH: 25
<212> TYPE: DNA
<213> ORGANISM: Artificial sequence
<220> FEATURE:
<223> OTHER INFORMATION: Primer

<400> SEQUENCE: 19
gggtcggagt ttttcggagt tgcgc                                            25

<210> SEQ ID NO 20
<211> LENGTH: 26
<212> TYPE: DNA
<213> ORGANISM: Artificial sequence
<220> FEATURE:
<223> OTHER INFORMATION: Primer

<400> SEQUENCE: 20
ccgctctctt cgctaaatac gactcg                                           26

<210> SEQ ID NO 21
<211> LENGTH: 48
<212> TYPE: DNA
<213> ORGANISM: Artificial sequence
<220> FEATURE:
<223> OTHER INFORMATION: Probe
```

<400> SEQUENCE: 21
cgacatgcgg tgtttcgttt tttcgcgttt tagtcgtcgg gcatgtcg        48

<210> SEQ ID NO 22
<211> LENGTH: 19
<212> TYPE: DNA
<213> ORGANISM: Artificial sequence
<220> FEATURE:
<223> OTHER INFORMATION: Primer

<400> SEQUENCE: 22
ggtcgtagtc gtagtcggg        19

<210> SEQ ID NO 23
<211> LENGTH: 21
<212> TYPE: DNA
<213> ORGANISM: Artificial sequence
<220> FEATURE:
<223> OTHER INFORMATION: Primer

<400> SEQUENCE: 23
ccgcaaaaac ctaaaacgta a        21

<210> SEQ ID NO 24
<211> LENGTH: 37
<212> TYPE: DNA
<213> ORGANISM: Artificial sequence
<220> FEATURE:
<223> OTHER INFORMATION: Probe

<400> SEQUENCE: 24
cgacatgcgg tttttgggt cggggcgcgg catgtcg        37

<210> SEQ ID NO 25
<211> LENGTH: 19
<212> TYPE: DNA
<213> ORGANISM: Artificial sequence
<220> FEATURE:
<223> OTHER INFORMATION: Primer

<400> SEQUENCE: 25
gagatgtttc gagggttgc        19

<210> SEQ ID NO 26
<211> LENGTH: 20
<212> TYPE: DNA
<213> ORGANISM: Artificial sequence
<220> FEATURE:
<223> OTHER INFORMATION: Primer

<400> SEQUENCE: 26
ccgcaatatc actaaaccga        20

<210> SEQ ID NO 27
<211> LENGTH: 43
<212> TYPE: DNA
<213> ORGANISM: Artificial sequence
<220> FEATURE:
<223> OTHER INFORMATION: Probe

<400> SEQUENCE: 27
cgacatgcgt tcgtgttttg gtttgtcgcg gtttggcatg tcg        43

```
<210> SEQ ID NO 28
<211> LENGTH: 22
<212> TYPE: DNA
<213> ORGANISM: Artificial sequence
<220> FEATURE:
<223> OTHER INFORMATION: Primer

<400> SEQUENCE: 28
tttttagatt tatcgagtgg cg                                              22

<210> SEQ ID NO 29
<211> LENGTH: 21
<212> TYPE: DNA
<213> ORGANISM: Artificial sequence
<220> FEATURE:
<223> OTHER INFORMATION: Primer

<400> SEQUENCE: 29
cgaactcacc tctctaccga c                                               21

<210> SEQ ID NO 30
<211> LENGTH: 33
<212> TYPE: DNA
<213> ORGANISM: Artificial sequence
<220> FEATURE:
<223> OTHER INFORMATION: Probe

<400> SEQUENCE: 30
cgacatgcca aaaacacgcc cccgcgcatg tcg                                  33

<210> SEQ ID NO 31
<211> LENGTH: 23
<212> TYPE: DNA
<213> ORGANISM: Artificial sequence
<220> FEATURE:
<223> OTHER INFORMATION: Primer

<400> SEQUENCE: 31
ttcgggttat tagcgttttt atc                                             23

<210> SEQ ID NO 32
<211> LENGTH: 19
<212> TYPE: DNA
<213> ORGANISM: Artificial sequence
<220> FEATURE:
<223> OTHER INFORMATION: Primer

<400> SEQUENCE: 32
actccaacca aacgacgaa                                                  19

<210> SEQ ID NO 33
<211> LENGTH: 35
<212> TYPE: DNA
<213> ORGANISM: Artificial sequence
<220> FEATURE:
<223> OTHER INFORMATION: Probe

<400> SEQUENCE: 33
cgacatcgtt ggttcggtgc gtgtggtcga tgtcg                                35

<210> SEQ ID NO 34
<211> LENGTH: 23
<212> TYPE: DNA
<213> ORGANISM: Artificial sequence
<220> FEATURE:
<223> OTHER INFORMATION: Primer
```

```
<400> SEQUENCE: 34
aatttgattt gtgtgtgtat cgc                                              23

<210> SEQ ID NO 35
<211> LENGTH: 22
<212> TYPE: DNA
<213> ORGANISM: Artificial sequence
<220> FEATURE:
<223> OTHER INFORMATION: Primer

<400> SEQUENCE: 35
gaaacgtaaa aatatcgtcg ca                                               22

<210> SEQ ID NO 36
<211> LENGTH: 44
<212> TYPE: DNA
<213> ORGANISM: Artificial sequence
<220> FEATURE:
<223> OTHER INFORMATION: Probe

<400> SEQUENCE: 36
cgacatgcgc gatttcggat ttattgcgtt gttagggcat gtcg                       44

<210> SEQ ID NO 37
<211> LENGTH: 20
<212> TYPE: DNA
<213> ORGANISM: Artificial sequence
<220> FEATURE:
<223> OTHER INFORMATION: Primer

<400> SEQUENCE: 37
gttcgttggg taaggcgttc                                                  20

<210> SEQ ID NO 38
<211> LENGTH: 22
<212> TYPE: DNA
<213> ORGANISM: Artificial sequence
<220> FEATURE:
<223> OTHER INFORMATION: Primer

<400> SEQUENCE: 38
cataaaacga acacccgaac cg                                               22

<210> SEQ ID NO 39
<211> LENGTH: 38
<212> TYPE: DNA
<213> ORGANISM: Artificial sequence
<220> FEATURE:
<223> OTHER INFORMATION: Probe

<400> SEQUENCE: 39
cgacatgcac cgcgcacctc ctcccgccaa gcatgtcg                              38
```